United States Patent
Cui et al.

(10) Patent No.: US 11,445,946 B2
(45) Date of Patent: Sep. 20, 2022

(54) PEDOT/CNT COATED NEURAL RECORDING PROBES FOR MEASUREMENT OF TONIC AND PHASIC DOPAMINE

(71) Applicant: University of Pittsburgh—Of the Commonwealth System of Higher Education, Pittsburgh, PA (US)

(72) Inventors: Xinyan Cui, Wexford, PA (US); Ian Mitchell Taylor, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 433 days.

(21) Appl. No.: 16/676,359

(22) Filed: Nov. 6, 2019

(65) Prior Publication Data

US 2020/0178864 A1    Jun. 11, 2020

Related U.S. Application Data

(60) Provisional application No. 62/757,055, filed on Nov. 7, 2018.

(51) Int. Cl.
| | |
|---|---|
| *A61B 5/145* | (2006.01) |
| *A61B 5/00* | (2006.01) |
| *G01N 27/30* | (2006.01) |
| *G01N 27/327* | (2006.01) |
| *B82Y 30/00* | (2011.01) |

(52) U.S. Cl.
CPC ........ *A61B 5/14546* (2013.01); *A61B 5/4064* (2013.01); *G01N 27/308* (2013.01); *G01N 27/3277* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 2013/0090542 A1* | 4/2013 | Kipke | A61B 5/24 607/116 |
| 2014/0316230 A1* | 10/2014 | Denison | A61B 5/168 600/545 |

OTHER PUBLICATIONS

R. Samba, et al., "Application of PEDOT-CNT Microelectrodes for Neurotransmitter Sensing", Electroanalysis, 26(3): p. 548-555, Mar. 2014.*
R. Gerwing, et al., "PEDOT-CNT composite microelectrodes for recording and electrostimulation applications: fabrication, morphology, and electrical properties", Frontiers in Neuroengineering, 5, Article 8, p. 1-11, May 2012.*
Alba, et al., "In Vivo Electrochemical Analysis of a PEDOT/MWCNT Neural Electrode Coating," *Biosensors* 5.4: 618-646, Oct. 2015.

(Continued)

*Primary Examiner* — J. Christopher Ball
(74) *Attorney, Agent, or Firm* — Klarquist Sparkman, LLP

(57) ABSTRACT

Disclosed herein is a method of determining dopamine concentration at a target location in neural tissue. In several embodiments, the method comprises measuring current level in response to square wave voltammetry with a coated electrode of a neural probe implanted at the target location, wherein the coated electrode comprises a coating of poly 3,4 ethylene dioxythiophene (PEDOT) doped with negatively charged carbon nanotubes (CNT), and comparing the measured current level to a control current level to determine the dopamine concentration at the target location.

18 Claims, 13 Drawing Sheets

(56) References Cited

OTHER PUBLICATIONS

Atcherley, et al., "The Coaction of Tonic and Phasic Dopamine Dynamics," *Chemical Communications* 51.12: 2235-2238, Feb. 2015.

Auclair, et al., "$_D$-Amphetamine Fails to Increase Extracellular Dopamine Levels in Mice Lacking Alpha 1b-Adrenergic Receptors: Relationship Between Functional and Nonfunctional Dopamine Release," *Journal of Neuroscience* 22.21: 9150-9154, Nov. 2002.

Bath, et al., "Subsecond Adsorption and Desorption of Dopamine at Carbon-Fiber Microelectrodes," *Analytical Chemistry* 72.24: 5994-6002, Dec. 2000.

Borland, et al., "Voltammetric Study of the Control of Striatal Dopamine Release by Glutamate," *Journal of Neurochemistry* 91.1: 220-229, Sep. 2004.

Carboni, et al., "Cocaine and Amphetamine Increase Extracellular Dopamine in the Nucleus Accumbens of Mice Lacking the Dopamine Transporter Gene," *The Journal of Neuroscience* 21: 1-4, 2001.

Du, et al., "Electrically Controlled Neurochemical Release from Dual-Layer Conducting Polymer Films for Precise Modulation of Neural Network Activity in Rat Barrel Cortex," *Advanced Functional Material* 28.12: 1-26, Mar. 2018.

Floresco, et al., "Afferent Modulation of Dopamine Neuron Firing Differentially Regulates Tonic and Phasic Dopamine Transmission," *Nature Neuroscience* 6.9: 968-973, Sep. 2003.

Gonon, et al., "Regulation of Dopamine Release by Impulse Flow and by Autoreceptors as Studied by In Vivo Voltammetry in the Rat Striatum," *Neuroscience* 14.3: 765-774, Mar. 1985.

Grace, "Dysregulation of the Dopamine System in the Pathophysiology of Schizophrenia and Depression," *Nature Reviews Neuroscience* 17.8: 524-532, Aug. 2016.

Grace, "Phasic Versus Tonic Dopamine Release and the Modulation of Dopamine System Responsivity: A Hypothesis for the Etiology of Schizophrenia," *Neuroscience* 41.1: 1-24, 1991.

Gu, et al., "In Vivo Monitoring of Dopamine by Microdialysis with One-Minute Temporal Resolution Using Online Capillary Liquid Chromatography with Electrochemical Detection," *Analytical Chemistry* 87.12: 6088-6094, Jun. 2015.

Hull, et al., "Hormone-Neurotransmitter Interactions in the Control of Sexual Behavior," *Behavioural Brain Research* 105.1: 105-116, Nov. 1999.

Jaquins-Gerstl, et al., "Comparison of the Brain Penetration Injury Associated with Mircodialysis and Voltammetry," *Journal of Neuroscience Methods* 183.2: 127-135, Oct. 2009.

Jaquins-Gerstl, et al., "The Effect of Dexamethasone on Gliosis, Ischemia, and Dopamine Extraction During Microdialysis Sampling in Brain Tissue," *Analytical Chemistry* 83.20: 7662-7667, Oct. 2011.

Johnson, et al., "Implantable Microelectrode Arrays for Simultaneous Electrophysiological and Neurochemical Recordings," *Journal of Neuroscience Methods* 174.1: 62-70, Sep. 2008.

Kozai, et al., "Chronic In Vivo Evaluation of PEDOT/CNT for Stable Neural Recordings," *IEEE Transactions on Biomedical Engineering* 63.1: 111-119, Jan. 2016.

Kozai, et al., "Brain Tissue Responses to Neural Implants Impact Signal Sensitivity and Intervention Strategies," *ACS Chemical Neuroscience* 6: 48-67, Dec. 2014.

Lourenco, et al., "Microelectrode Array Biosensor for High-Resolution Measurements of Extracellular Glucose in the Brain," *Sensors and Actuators B: Chemical*, 237: 298-307, Jun. 2016.

Luo, et al., "Highly Stable Carbon Nanotube Doped Poly(3,4-Ethylenedioxythiophene) for Chronic Neural Stimulation," *Biomaterials* 32.24: 5551-5557, Aug. 2011.

Nesbitt, et al., "Microdialysis in the Rat Striatum: Effects of 24 h Dexamethosaone Retrodialysis on Evoked Dopamine Release and Penetration Injury," *ACS Chemical Neuroscience* 6.1: 163-173, Jan. 2015.

Nesbitt, et al., "Pharmacological Mitigation of Tissue Damage During Brain Microdialysis," *Analytical Chemistry* 85.17: 8173-8179, Sep. 2013.

Obien, et al., "Revealing Neuronal Function Through Microelectrode Array Recordings," *Frontiers in Neuroscience* 8: 1-30, Jan. 2015.

Oh, et al., "Tracking Tonic Dopamine Levels In Vivo Using Multiple Cyclic Square Wave Voltammetry," *Biosensors and Bioelectronics* 121: 174-182, Dec. 2018.

Park, et al., "In Vivo Comparison of Norepinephrine and Dopamine Release in Rat Brain by Simultaneous Measurements with Fast-Scan Cyclic Voltammetry," *Journal of Neurochemistry* 119.5: 932-944, Dec. 2011.

Pontieri, et al., "Intravenous Cocaine, Morphine, and Amphetamine Preferentially Increase Extracellular Dopamine in the "Shell" as Compared with the "Core" of the Rat Nucleus Accumbens," *Proceedings of the National Academy of Sciences of the United States of America* 92.26: 12304-12308, Dec. 1995.

Rassoulpour, et al., "Nanomolar Concentrations of Kynurenic Acid Reduce Extracellular Dopamine Levels in the Striatum," *Journal of Neurochemistry* 93.3: 7626-765, May 2005.

Robinson, et al., "Detecting Subsecond Dopamine Release with Fast-Scan Cyclic Voltammetry in Vivo," *Clinical Chemistry* 49.10: 1763-1773, Oct. 2003.

Rutherford, et al., "Chronic Second-by-Second Measures of $_L$-glutamate in the Central Nervous System of Freely Moving Rats," *Journal of Neurochemistry* 102.3: 712-722, Aug. 2007.

Schultz, "Multiple Dopamine Functions at Different Time Courses," *Annual Review of Neuroscience* 30: 259-288, Mar. 2007.

Schultz, "Predictive Reward Signal of Dopamine Neurons," *Journal of Neurophysiology* 80.1: 1-27, Jul. 1998.

Taylor, et al., "Aptamer-Functionalized Neural Recording Electrodes for the Direct Measurement of Cocaine in vivo," *Journal of Materials Chemistry B* 5.13: 2445-2458, Apr. 2017.

Taylor, et al., "Domain-Dependent Effects of Dat Inhibition in the Rat Dorsal Striatum," *Journal of Neurochemistry* 122.2: 283-294, Jul. 2012.

Taylor, et al., "Enhanced Dopamine Detection Sensitivity by PEDOT/Graphene Oxide Coating on in vivo Carbon Fiber Electrodes," *Biosensors and Bioelectronics* 89: 400-410, Mar. 2017.

Taylor, et al., "Kinetic Diversity of Dopamine Transmission in the Dorsal Striatum," *Journal of Neurochemistry* 133.4: 522-531, May 2015.

Taylor, et al., "Restricted Diffusion of Dopamine in the Rat Dorsal Striatum," *ACS Chemical Neuroscience* 4.5: 870-878, May 2013.

Taylor, et al., "PEDOT-based electrode coatings for high sensitivity detection of tonic and phasic dopamine in vivo." Society for Neuroscience 2017 National Convention. Washington DC, Nov. 13, 2017.

Taylor, et al., "PEDOT/carbon nanotube functionalized micro electrodes for real-time electrochemical detections of resting dopamine." Pittsburgh Conference for Analytical Chemistry. Orlando, FL, Feb. 2018.

Tseng, et al., "Implantable Microprobe with Arrayed Microsensors for Combined Amperometric Monitoring of the Neurotransmitters, Glutamate and Dopamine," *Journal of Electroanalytical Chemistry* 682: 141-146, Aug. 2012.

Urban, et al., "Imaging Human Reward Processing with Positron Emission Tomography and Functional Magnetic Resonance Imaging," *Psychopharmacology* 221.1: 67-77, May 2012.

Vasylieva, et al., "Silicon/SU8 Multi-Electrode Micro-Needle for in vivo Neurochemical Monitoring," *Biosensors and Bioelectronics* 72: 148-155, Oct. 2015.

Weaver, et al., "A Graphene Oxide/Conducting Polymer Nanocomposite for Electrochemical Dopamine Detection: Origin of Improved Sensitivity and Specificity," *Journal of Materials Chemistry B* 2.32: 1-11, Jun. 2014.

Xu, et al., "Electrodeposited Conducting Polymer PEDOT Doped with Pure Carbon Nanotubes for the Detection of Dopamine in the Presence of Ascorbic Acid," *Sensors and Actuators B* 188: 405-410, Jul. 2013.

* cited by examiner

FIG. 1A
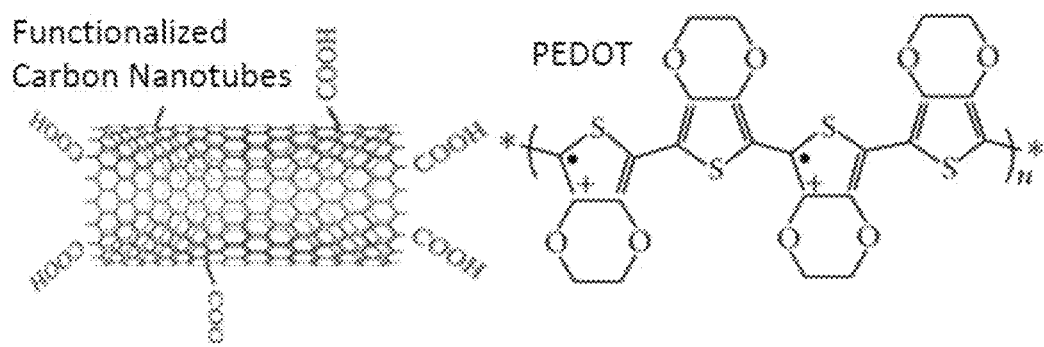
FIG. 1B
Uncoated CFE
FIG. 1C
PEDOT/fCNT coated CFE
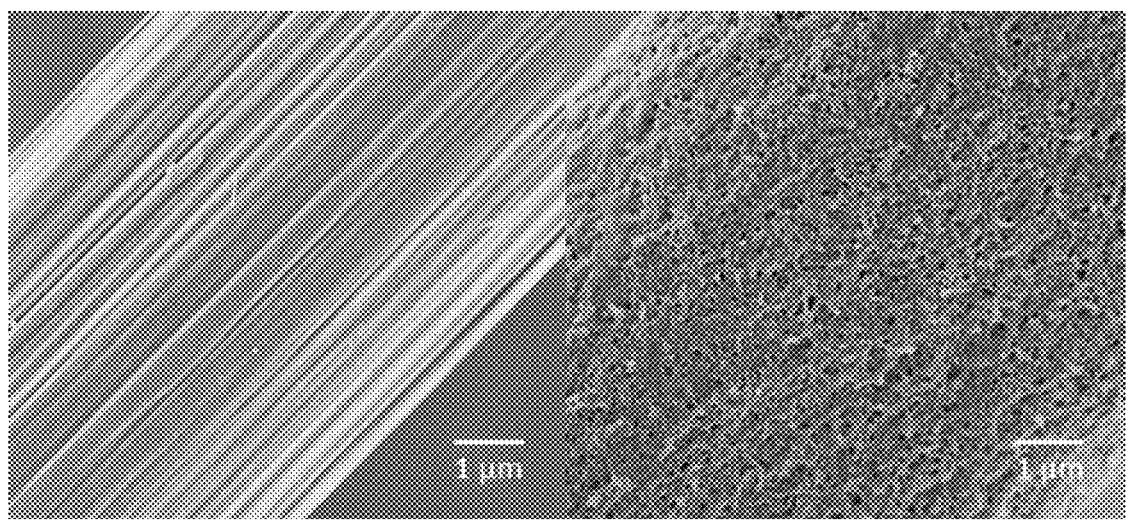

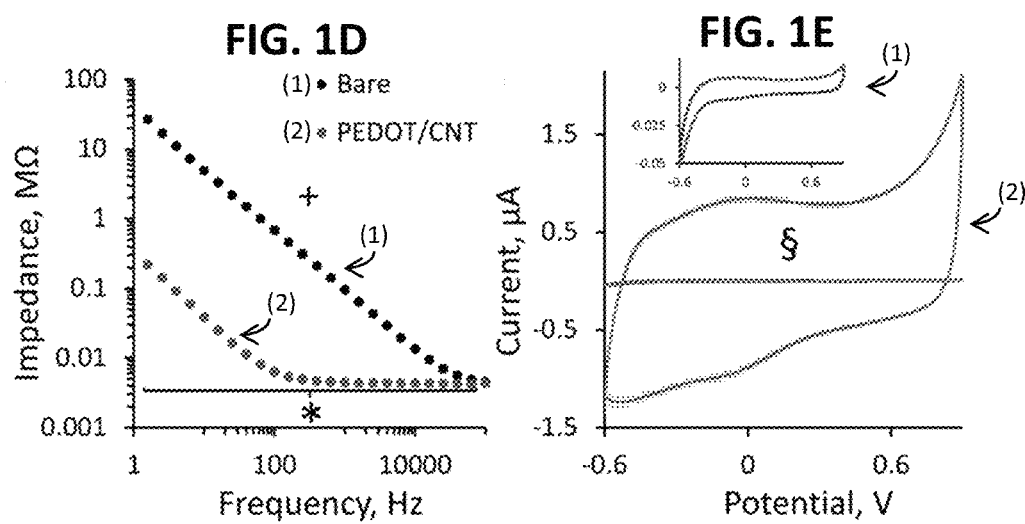
In vitro characterization of sensor performance of CFE coated with varying thickness of PEDOT/fCNT (1) Anodic hold period
(2) Stair step waveform
(3) Cathodic hold period

*In vivo* Acute DA detection

PEDOT/CNT COATED NEURAL RECORDING PROBES FOR MEASUREMENT OF TONIC AND PHASIC DOPAMINE

CROSS REFERENCE TO RELATED APPLICATION

This application claims the benefit of U.S. Provisional Application No. 62/757,055, filed Nov. 7, 2018, which is incorporated herein by reference in its entirety.

ACKNOWLEDGMENT OF GOVERNMENT SUPPORT

This invention was made with government support under Grant Nos. NS062019, DA049592, and DA043817 awarded by the National Institutes of Health. The government has certain rights in the invention.

FIELD

The present disclosure relates to the field of determining dopamine concentration in neural tissue.

BACKGROUND

Dopamine (DA) signaling over multiple time courses is responsible for the regulation of a variety of vital life functions. Extracellular dopamine vary depending on changes in the kinetics of dopamine release and uptake and are highly correlated to physiological functionality. Extracellular dopamine has been measured for decades with carbon fiber microelectrodes using electrochemical detection techniques, such as fast scan cyclic voltammetry. Although electrochemical detection at bare carbon fibers has proven quite successful over decades of use, these techniques are limited by issues resulting from moderate sensitivity, poor sensor longevity, and the inability to measure resting DA concentrations.

SUMMARY

Provided herein is a novel method for determining dopamine concentration in neural tissue. The method comprises measuring current level in response to square wave voltammetry with a neural probe implanted at a target location in the neural tissue. The neural probe comprises one or more electrodes (for example, carbon-fiber electrodes or gold electrodes) with a coating of poly 3,4 ethylene dioxythiophene (PEDOT) doped with negatively charged carbon nanotubes (CNT). The measured current level is compared to a control current level (for example, a current level measured for a known concentration of dopamine in response to square wave voltammetry applied with a control electrode) to determine the dopamine concentration at the target location. The method is surprisingly effective for determining the tonic (resting) dopamine concentration at the target location in the neural tissue.

In some embodiments, the CNTs in the PEDOT/CNT coat are carbon nanotubes modified to have a negative charge by acid treatment. In some embodiments, the CNTs in the PEDOT/CNT coat are from about 10 to about 20 nm in diameter and from about 10 to about 30 µm in length. In some embodiments, the PEDOT/CNT coat is electrodeposited onto the one or more electrodes of the neural probe. For example, in some embodiments, the PEDOT/CNT coat is electrodeposited on the one or more electrodes of the neural probe at a thickness of from about 5 to about 200 $mC/cm^2$, such as about 100 $mC/cm^2$.

In some embodiments, the square wave voltammetry comprises sweeps performed at 25 Hz and lasting for about 3 seconds in length. In some embodiments, the sweeps of the square wave voltammetry comprise from about −0.2 to about 0.3 volts, such as about 0.18 volts.

In some embodiments, the target location in the neural tissue is neural tissue with a norepinephrine concentration of less than 1 µM. Non-limiting examples include any one of the dorsal striatum, nucleus accumbens core, nucleus accumbens shell, prefrontal cortex, or amygdala.

In several embodiments, the method further comprises implanting the neural probe at the target location. In some embodiments, the method further comprises connecting the probe to a recording apparatus via one or more electrical leads; and recording and/or stimulating the neural signal from the neuronal tissue.

The foregoing and other objects, features, and advantages of the embodiments will become more apparent from the following detailed description, which proceeds with reference to the accompanying figures.

BRIEF DESCRIPTION OF THE FIGURES

FIGS. 1A-1E. Uniform PEDOT/CNT electrodeposition onto carbon fiber electrodes (CFEs) significantly decreases impedance. (FIGS. 1A-1C) CNT-doped PEDOT was electrodeposited onto CFE. 1000× magnification scanning electron microscopy images of representative bare (FIG. 1B) and 100 $mC/cm^2$ PEDOT/CNT functionalized (FIG. 1C) CFEs reveals in a uniform high surface area "birds nest morphology" coating. (FIG. 1D) Average electrode impedance (±SEM, n=5) significantly changes with PEDOT/CNT coating, frequency and those two variables exhibit a significant interaction (+2-way ANOVA with repeated measures design, Coating: $F (1.19, 9.54)=1032$, $p<1E-9$; Frequency: $F (1.19, 9.54)=424$, $p<2E-9$; Interaction: $F (1.19, 9.54)=410$, $p<5E-9$;). Furthermore PEDOT/CNT significantly decreases average impedance at each individual frequency below 100 kHz (* Bonferroni post hoc analysis, $p<0.05$). (FIG. 1E) PEDOT/CNT coating significantly increases the average amplitude of the nonfaradaic charging current in response to a 1 V/sec CV sweep (±SEM dashed lines, n=5) from an 0.067±0.003 µA to 3.40±0.09 µA (inset displays the average bare response (±SEM, § 1-way ANOVA, $F (1, 9)=1852$, $p<1E-10$).

(FIG. 2D) Illustration of chemical change to dopamine to generate a measurable current. (FIG. 2E) Representative SWV measurement of a 1 µM standard solution of DA at a PEDOT/CNT functionalized CFE reveals a clear oxidation peak for the transition from DA to DAoQ in the forward scan and a clear reduction peak for the transition from DAoQ to DA in the backward scan. (f) The final SWV current response manifests as a single current peak reflecting the difference between the forward and backward current responses. (FIG. 2G) Increasing PEDOT/CNT thickness increases the sensitivity for dopamine.

(FIG. 3A) Average (n=5, SEM omitted for clarity) in vitro SWV DA calibrations conducted at PEDOT/CNT functionalized CFEs in artificial cerebrospinal fluid (aCSF) reveal clear peaks at 0.18 V due to the electrochemical detection of DA. (FIG. 3B) Subtraction of the aCSF baseline SWV response reveals clear, concentration dependent gaussian peaks. (FIG. 3C) The peak current associated with DA detection using SWV is linearly correlated ($r^2$>0.99), and the integration of PEDOT/CNT coating significantly increases the sensitivity for DA detection from 0.000086±0.000062 nA/nM (n=3) in bare CFEs to 0.104±0.009 nA/nM (n=5) following PEDOT/CNT coating (*One-way ANOVA, p<0.05). (FIG. 3D) Average (n=5, SEM omitted for clarity) in vitro SWV DA calibrations conducted at PEDOT/CNT functionalized CFEs in the presence of a cocktail of common neurochemical interferents consisting of 200 µM ascorbic acid (AA), 10 µM uric acid (UA) and 10 µM DOPAC (pH adjusted to 7.4) reveal clear DA peaks at 0.18 V. (FIG. 3E) The $2^{nd}$ order polynomial fit (dashed) was capable of modelling the baseline SWV response resulting from the interferents within the potential region of interest both in the presence (250 nM DA, green) and absence (blue) of DA. (FIG. 3F) Average DA sensitivity in the presence of interferents is linearly correlated. Incorporation of interferents does not produce a significant difference (One-way ANOVA, p>0.05, compared to FIG. 4C) in average DA sensitivity using SWV.

(FIG. 4A) A $2^{nd}$ order polynomial was used to model the background current for each SWV response within the potential region of interest (surrounding $E_{peak}$ 0.18 V). The polynomial fit (dashed) produces a high correlation fit within the potential region of interest to individual SWV traces (average SWV responses shown) both in the presence (250 nM DA, green) and absence (aCSF) of DA. (FIG. 4B) Subtraction of the polynomial baseline fit reveals clear concentration dependent Gaussian peaks (average±SEM) for solutions containing DA and nearly flat baselines in solutions where DA is absent. (FIG. 4C) Average DA sensitivity (background subtracted peak current vs DA concentration) is linearly correlated. Incorporating PEDOT/CNT coating significantly increases DA sensitivity (*One-way ANOVA, p<0.05) from bare CFEs. Average sensitivity of PEDOT/CNT functionalized CFEs following polynomial background subtraction is not significantly different from the sensitivity obtained via aCSF subtraction (One-way ANOVA, p>0.05).

(FIG. 6A) SWV measurement at PEDOT/CNT functionalized CFEs reveal clear Gaussian DA peaks in the rat dorsal striatum (n=3 average) but not in the non-DA-rich forelimb region of the primary somatosensory cortex (S1FL, n=3 average). (FIG. 6B) Average in vivo DA concentration (±SEM) was plotted over time before and after i.p. administration of 20 mg/kg nomifensine (plot labeled (1), n=3 individual rats) or saline vehicle control (plot labeled (2), n=3 individual rats) at t=30 minutes (vertical dashed line). Basal DA was quantified on average to be 82±6 nM (n=6 individual rats) and nomifensine administration results in increased DA concentration beginning approximately 5 minutes following i.p. injection and increasing until reaching an average maximum DA concentration of 207±16 nM at 28±2 minutes following drug administration.

(FIG. 7A) 40× bright field microscopy imaging clearly displays that PEDOT/CNT selectively deposits onto the surface of individual 1200 µm² gold electrodes located along silicon MEAs following 100 mC/cm² chronocolometry electrodeposition. (FIG. 7B) Average (n=5, SEM omitted for clarity) in vitro SWV DA calibrations conducted at PEDOT/CNT functionalized MEAs in aCSF reveal clear, concentration dependent peaks at 0.18 V due to the electrochemical detection of DA. aCSF subtraction reveals the average (±SEM) peaks to be gaussian in shape (inset). (FIG. 7C) PEDOT/CNT functionalized MEAs exhibit a linear increase in average peak current (±SEM) with increased DA concentration corresponding to a 0.0147±0.0005 nA/µM average sensitivity. Uncoated gold MEA sites (±SEM, n=5, isolated view shown in inset) are completely insensitive for DA detection. Average sensitivity at bare gold MEAs is both nonlinear and negative, –0.000024±0.000029 nA/µM. PEDOT/CNT nanocomposite coatings significantly increase MEA sensitivity for DA (*One-way ANOVA, p<0.05).

DETAILED DESCRIPTION

I. Introduction

Figure 2A:
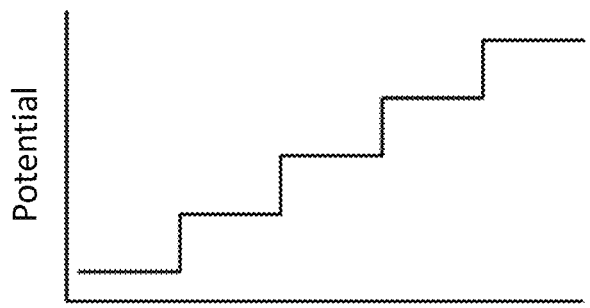
FIGS. 2A-2G. SWV waveform construction and DA detection. A SWV waveform consists of the combination of a stair step waveform (FIG. 2A) and a square wave waveform (FIG. 2B), where the amplitude, frequency and start and stop potentials are defined by the user. The resulting SWV waveform (FIG. 2C) consists of a series of anodic and cathodic step and holds that transverse a potential window defined by stair step waveform (markers labeled (2)). Forward current is measured at the end of each anodic hold period (markers labeled (1)) and backward current is measured at the end of each cathodic hold period (markers labeled (3)).
Figure 2B:
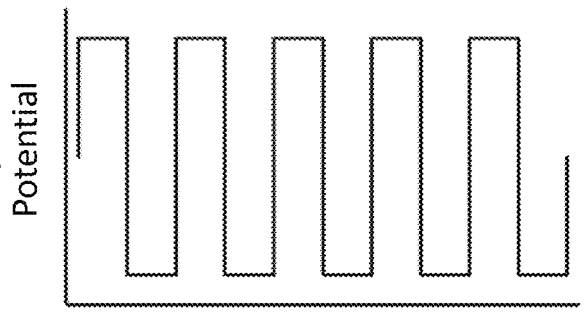
Figure 2C:
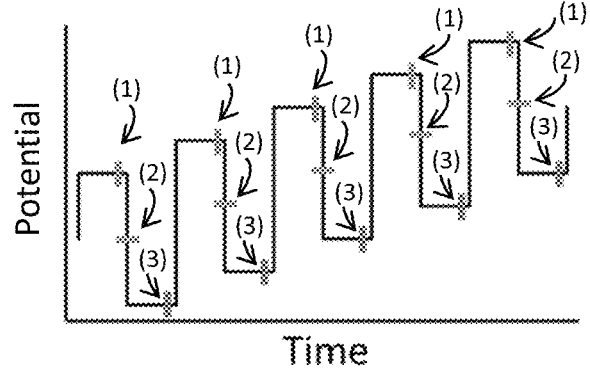

As disclosed herein, PEDOT/CNT coated neural recording probes are capable of directly measuring resting and phasic DA using square wave voltammetry (SWV) with high sensitivity and selectivity at multiple discrete brain regions. For example, incorporation of a 100 mC/cm² PEDOT/CNT coating onto gold microelectrode sites along neural recording probes significantly decreased the overall electrode impedance over 5 frequency decades and transformed previously DA insensitive gold electrode sites in highly sensitive DA recording sites. In addition, PEDOT/CNT coated electrodes are selective for DA over common neurochemical interferents found in the brain, including ascorbic acid. Further, SWV measurements performed at PEDOT/CNT coated neural recording electrodes implanted in the rat dorsal striatum reveal the absolute basal DA concentration as well as location specific changes in tonic DA upon systemic injection of the dopamine transporter inhibitor, nomifensine.

The novel electrochemical sensor technology provided herein represents the first ever electrode technology capable of directly measuring both tonic and phasic DA. In addition, PEDOT/CNT coated neural recording probes exhibit the highest spatial and temporal resolution for the direct quantification of resting DA concentration. In some embodiments, a multimodal DA sensor provides an unparalleled amount of information regarding the spatio-temporal dynamics of DA signaling in vivo, which will be of great utility in a wide range of neuroscience implementations.

II. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the term "comprises" means "includes." It is further to be understood that all molecular weight or molecular mass values are provided for descriptive purposes, unless otherwise indicated. Although many methods and materials similar or equivalent to those described herein can be used, particular suitable methods and materials are described below. In addition, the materials, methods, and examples are illustrative only and not intended to be limiting. The scope of the claims should not be limited to those features exemplified. To facilitate review of the various embodiments, the following explanations of terms are provided:

About: Unless context indicated otherwise, "about" refers to plus or minus 5% of a reference value. For example, "about" 100 refers to 95 to 105.

Coat: A layer of material that partially or fully covers a surface. For example, a PEDOT/CNT layer can fully coat an exterior surface of an electrical conductor to facilitate detection of DA by the conductor.

Coated electrode: An electrode with a layer of material that partially or fully covers the conductive surface (or surfaces) of the electrode. The layer of material is itself conductive. For example, a conductive polymer can be electrodeposited on the conductive surface of an electrode to generate an electrode coated with the conductive polymer. The conductive surface of the electrode does not need to be completely coated (and in many cases is partially coated). Further, the amount of coating can vary according to the application parameters, e.g., time of use, exposure, level of signals, levels of noise, desired compound density, etc. The coat or coating on a coated electrode is the layer of material that partially or fully covers the conductive surface (or surfaces) of the electrode.

Doping and Dopants: Doping is the process of oxidizing (p-doping) or reducing (n-doping) a neutral polymer and providing a counter anion or cation (the dopant). Doping can also occur during electropolymerization process, in which monomers are oxidized and polymerized into charged long chain molecules while counter ions nearby incorporated via electrostatic force. Typically, upon doping, a conductive polymer system with a net charge of zero is produced due to the close association of the counterions with the charged conductive polymer backbone. In some examples, dopants can catalyze the polymerization of monomers during synthesis. In several examples, the disclosed embodiments include negatively charged carbon nanotubes as dopants in a PEDOT conductive polymer, which alters the conductive properties of the polymer. The negatively charged carbon nanotubes interact with the positive charge of the conductive polymer backbone. A "doped" conductive polymer is a conductive polymer including a dopant.

Electrode: An electric conductor through which an electric current can pass. An electrode can also be a collector and/or emitter of an electric current. In some embodiments, an electrode is a solid and comprises a conducting metal as the conductive layer. Non-limiting examples of conducting metals include noble metals and alloys, such as stainless steel and tungsten. An "array of electrodes" refers to a device with at least two electrodes formed in any pattern. The electrodes can be either interconnected or independently wired.

Effective amount: The "effective amount" of a composition or agent is the quantity of the composition or agent sufficient to achieve a desired result.

Implanting: Completely or partially placing a neural probe or device including a neural probe within a subject, for example, using surgical techniques. A device or probe is partially implanted when some of the device or probe reaches, or extends to the outside of, a subject. Implantable probes and devices may be implanted into neural tissue, such as the central nervous system, more particularly the brain, for treatment of different medical conditions and for various time periods. A neural probe or device can be implanted for varying durations, such as for a short term duration (e.g., one or two days or less) or for long-term or chronic duration (e.g., one month or more).

Neural probe: A device or component of a device including one or more electrodes that can be placed in contact with neuronal tissue (e.g., in an animal host) and can record and/or stimulate neural signals from or to the neuronal tissue. Neural probes typically include conductive and non-conductive surfaces designed for contact with neuronal tissue when implanted at a target location in a subject, and can include one or more electrodes that can be independently monitored from other conductive surfaces on or off the probe) for recording current at the target location. In several embodiments, probes for use in the disclosed methods are included in a device (such as an array or a deep brain stimulator) for recording and/or stimulating a neural signal in a subject.

Subject: Living multi-cellular vertebrate organisms, a category that includes human and non-human mammals, including non-human primates, rats, mice, guinea pigs, cats, dogs, cows, horses, and the like. Thus, the term "subject" includes both human and veterinary subjects.

III. Determining Dopamine Levels in Neural Tissue

Provided herein is a method for determining dopamine concentration at a target location in neural tissue. The method comprises measuring current level in response to square wave voltammetry with a PEDOT/CNT coated electrode of a neural probe implanted at the target location, and comparing the measured current level to a control current level to determine the dopamine concentration at the target location.

In several embodiments, the method is used to determine the tonic dopamine concentration at the target location in the neural tissue.

The target location can be any appropriate site in the neural tissue containing dopamine. For example, the target location can be any one of the dorsal striatum, the nucleus accumbens (e.g., the nucleus accumbens core or shell), the prefrontal cortex, or the amygdala. In some embodiments, the target location is neural tissue with a norepinephrine concentration of less than 1 µM.

The neural tissue can be from any suitable subject, such as a human. In some embodiments, the neural tissue is in vivo. In other embodiments, the neural tissue has been removed from a subject for assessment with the methods provided herein. In still more embodiments, the neural tissue is engineered or artificial tissue designed to mimic one or more properties of neural tissue from a subject, such as one or more properties pertaining to dopamine in neural tissue from a subject.

The neural probe implanted at the target location of the neural tissue can be any suitable neural probe for implantation into neural tissue. For example, the neural probe can be designed for temporary or permanent implantation into the neural tissue of a subject. In some embodiments, the neural probe is designed for implantation into neural tissue excised from a subject, and/or artificial neural tissue prepared in a laboratory. Non-limiting examples of types of neural probes for use in the methods provided herein include silicon-based, flexible polymer (polyimide, SU-8, parylene C, shape memory polymer, polymer nanocomposite) based, ceramics (silicon carbide, alumina or diamond) based, and metal microwire based multichannel neural electrode arrays and carbon fiber arrays.

The neural probe implanted at the target location of the neural tissue includes one or more electrodes that can be placed in contact with neuronal tissue (e.g., in an animal host) and can record current at the target location in the neuronal tissue. Neural probes typically include conductive and non-conductive surfaces designed for contact with neuronal tissue when implanted in a subject, and can include one or more electrodes that can be independently monitored from other conductive surfaces on or off the probe) for recording current at the target location. In several embodiments, probes for use in the disclosed methods are included in a device (such as an array) for recording current at one or more target locations in neural tissue.

The neural probe implanted at the target location of the neural tissue comprises one or more electrodes with an effective amount of a PEDOT/CNT coating on their exterior surface that is implanted into the neural tissue. The electrodes do not need to be completely coated with the PEDOT/CNT; in many examples a partial coating is sufficient. The amount of PEDOT/CNT included in a "PEDOT/CNT-coat" on the external surface of a probe can vary according to the application parameters, e.g., time of use, exposure, level of signals, levels of noise, desired PEDOT/CNT density, etc. The effective amount of the PEDOT/CNT-coat is an amount sufficient to improve the DA-sensing capability relative to a control uncoated electrode in the methods provided herein.

Conductive polymers such as PEDOT can be controllably deposited on a substrate surface via the application of a potential sufficient to oxidize and polymerize the specific monomer. The introduction of a thin conductive polymer film increases the effective surface area in addition to incorporating a specific reactive surface on the electrode substrate without sacrificing the conductive property of the electrode. Poly(3,4-ethylene dioxythiophene) (PEDOT) can be electro-polymerized from 3,4-ethylene dioxythiophene (EDOT) monomers. The oxidative polymerization of PEDOT results in positive charges on the polymer backbone, which allows for the incorporation of negatively charged doping agents, such as CNTs modified (that is, "functionalized") to have a negative charge.

The CNTs in the coating can be any appropriate size. In some example, the CNTs are from about 10 to about 20 nm in diameter and from about 10 to about 30 µm in length. The CNTs for use in the embodiments provided herein are "functionalized" CNTs that are CNTs modified to facilitate doping of the PEDOT in the PEDOT/CNT coat. In several embodiments, the CNTs are CNTs modified to have a negative charge, for example by treatment with acid.

Any appropriate technique can be used to coat the one or more electrodes of the neural probe with the PEDOT/CNT coating. Non-limiting examples include coating methods such as electrodeposition, dipping, spraying, painting, vacuum deposition, and conjugation to the one or more electrodes of the probe. Exemplary methods of applying a PEDOT/CNT coat to an electrode are provided in Alba et al., Biosensors 5, 618, 2015, Kozai et al., *IEEE transactions on bio-medical engineering*, 63, 111-119, 2016, Luo et al., *Biomaterials*, 32, 5551-5557, 2011, Taylor et al., *Biosens Bioelectron*, 89, Part 1, 400-410, 2017b, and Xu et al., *Sensors Actuators B: Chem*, 188, 405-410, 2013, each of which is incorporated by reference herein.

In some embodiments, the PEDOT/CNT coating is electrodeposited onto the electrodes of the neural probe. For example, the one or more electrodes of the neural probe are coated with PEDOT/CNT electrodeposited at from about 5 to about 200 mC/cm$^2$ (for example, from about 5 to about 200 mC/cm$^2$, from about 5 to about 150 mC/cm$^2$, from about 5 to about 100 mC/cm$^2$, from about 100 to about 200 mC/cm$^2$, from about 10 to about 200 mC/cm$^2$, from about 10 to about 150 mC/cm$^2$, from about 50 to about 150 mC/cm$^2$, or from about 80 to about 120 mC/cm$^2$). In some embodiments, the one or more electrodes of the neural probe are coated with PEDOT/CNT electrodeposited at about 25 mC/cm$^2$, about 75 mC/cm$^2$, about 100 mC/cm$^2$, about 125 mC/cm$^2$, about 150 mC/cm$^2$, or about 175 mC/cm$^2$.

The one or more electrodes in the neural probe can be any suitable electrode that is amenable to coating with the PEDOT/CNT coat provided herein, and that can be used to record current at the target location of the neural tissue. In some embodiments, the electrode is a carbon-fiber electrode or a gold electrode.

The method for determining dopamine concentration provided herein includes measuring current level in response to square wave voltammetry with a PEDOT/CNT coated electrode of a neural probe implanted at a target location of neural tissue, and comparing the measured current level to a control current level to determine the dopamine concentration at the target location. SWV is a form of linear potential sweep voltammetry that uses a combined square wave and staircase potential applied to a working electrode. The current at the working electrode is measured while the potential between the working electrode and a reference electrode is swept linearly in time. The potential waveform can be viewed as a superposition of a regular squarewave onto an underlying staircase (see FIG. 2).

Figure 2D:
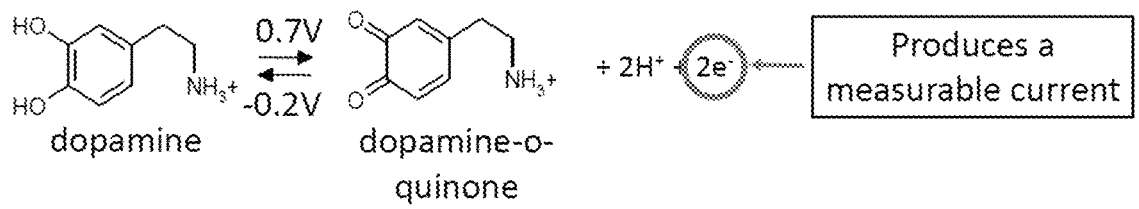
Figure 2E:
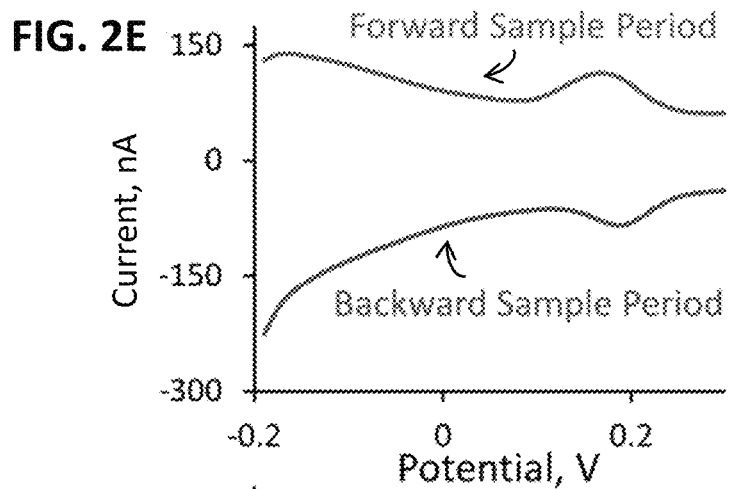
Figure 2F:
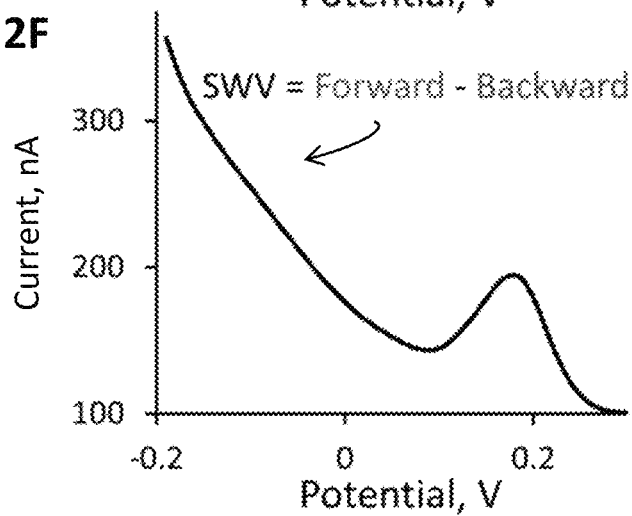
Figure 2G:
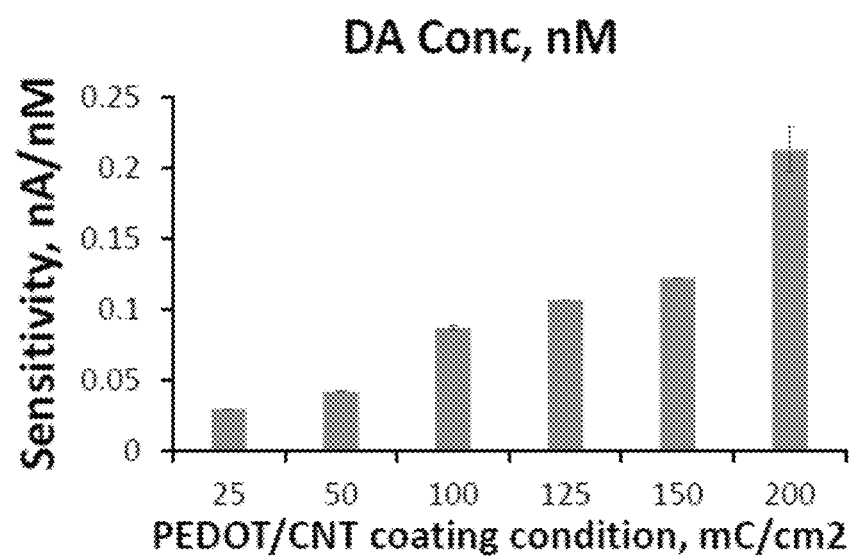
Figure 3A:
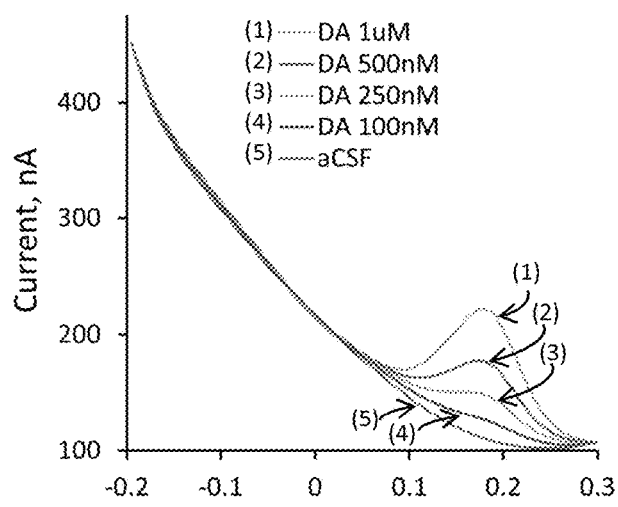
FIGS. 3A-3F. PEDOT/CNT functionalized CFEs are sensitive and selective for resting DA.
Figure 3B:
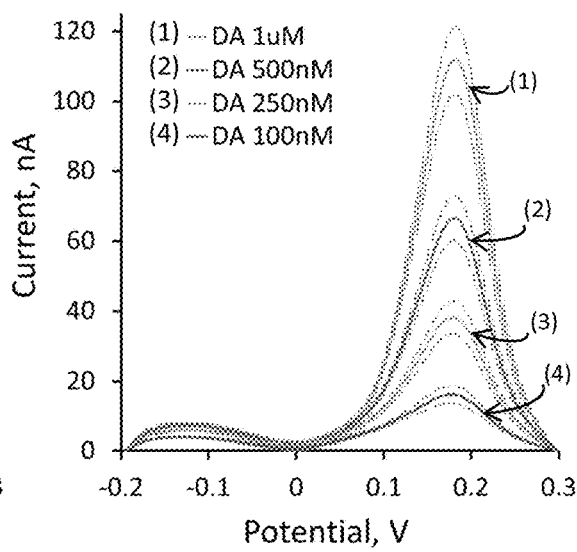

The current is typically sampled at two times—once at the end of a forward potential pulse and again at the end of a reverse potential pulse (see FIG. 2E). The SWV waveform is derived by subtracting the reverse current waveform from the forward current waveform (FIG. 2F). This differential curve is then plotted against the applied potential. Peaks in the differential current vs. applied potential plot are indicative of redox processes, and the magnitudes of the peaks in this plot are proportional to the concentrations of the redox active species. As shown in FIG. 2D, the redox chemistry of dopamine produces a measurable current, which (as shown in FIG. 3B) forms a peak at about 0.18 volts.

In some embodiments, sweeps of the square wave voltammetry are performed at 25 Hz and lasting for about 3 seconds in length. In some embodiments, the sweeps of the square wave voltammetry are from about −0.2 to about 0.3 volts. In some embodiments, the current level measured in response to application of from about −0.2 to about 0.3 volts with the neural probe is compared with the control current level to determine the dopamine concentration in the neural tissue.

In some embodiments, the control current level is a current level measured for a known concentration of dopamine in response to square wave voltammetry applied with a control electrode. In some embodiments, the current level measured in response to application of about 0.18 volts with the neural probe is compared with the control current level to determine the dopamine concentration in the neural tissue.

The neural probe is typically linked to recording and/or stimulating circuitry. In some in vivo embodiments, the circuitry can be integrated circuitry that is fully implanted (typically implantable in a subcutaneous pocket within a patient's body) or partially implanted in the patient. Linkage of the circuitry to the probe can be by way of one or more leads, although any operable linkage capable of transmitting the measured neural signal from the electrodes to the circuitry, or a stimulation signal from the circuitry to the electrodes, can be used.

EXAMPLES

The following examples are provided to illustrate particular features of certain embodiments, but the scope of the claims should not be limited to those features exemplified.

Example 1

Direct In Vivo Electrochemical Detection of Resting Dopamine Using PEDOT/CNT Coated Carbon Fiber Microelectrodes Dopamine (DA) is a monoamine neurotransmitter responsible for the maintenance of a variety of vital life functions. In vivo DA signaling occurs over multiple time scales. Phasic DA release induces sub second transient concentration fluctuations whereas tonic firing maintains local basal DA concentration and is responsible for long-term DA concentration changes occurring over minutes to hours. Due to the complex, multifaceted nature of DA signaling, analytical sensing technology must be capable of recording DA from multiple locations and over multiple timescales. Decades of research has focused on improving in vivo detection capabilities for sub-second phasic DA, but the accurate detection of absolute resting DA levels has proven challenging. We have developed a poly (3,4 ethylene dioxythiophene) (PEDOT)-based nanocomposite coating that exhibits excellent DA sensing capabilities for resting DA. PEDOT/carbon nanotube (PEDOT/CNT) coated carbon fiber microelectrodes (CFEs) are capable of directly measuring resting DA using square wave voltammetry (SWV) with high sensitivity and selectivity. Incorporation of a 100 mC/cm$^2$ PEDOT/CNT coating significantly decreases the overall electrode impedance over 5 frequency decades which results in a 520% significant increase in sensitivity for the detection of resting DA using SWV. In addition, SWV measurements at PEDOT/CNT coated CFEs exhibit clear peak separation between common neurochemical interferents, including ascorbic acid (AA). SWV measurements performed at PEDOT/CNT coated CFEs implanted in the rat dorsal striatum reveal that the absolute basal DA concentration to be 250±17 nM and that systemic administration of the dopamine transporter inhibitor, nomifensine increases resting DA to a maximum 515±45 nM at 28±2 minutes following injection. PEDOT/CNT also converts previously DA insensitive gold electrode sites along silicon microelectrode arrays (MEAs) into highly sensitive DA sensing electrodes. DA. MEA implantation allows for the quantification of basal DA with excellent spatial resolution. This study introduces an exciting new electrode coating/voltammetric methodology that is highly adaptable and shows great promise for the direct detection of tonic DA.

Introduction

Tonic and phasic dopamine (DA) neurotransmission are responsible for the regulation of a myriad of vital life functions. Phasic DA release induces transient, sub-second fluctuations in extracellular DA responsible for controlling conditioned stimuli, whereas tonic firing maintains basal DA levels that serve to regulate phasic firing and control various motor and cognitive functions. It is widely believed that preserving tonic and phasic firing is key to maintaining healthy neuronal functionality. Disfunction in the regulation of tonic and phasic DA firing has been implicated in the onset of devastating neurological disorders, such as schizophrenia. As such, it is preferred to consider both tonic and phasic DA signaling events when studying DA signaling pathways.

DA is an electroactive compound capable of reversible oxidation to dopamine-o-quinone (DAoQ) upon application of a sufficient potential. Electrochemical measurement of the current associated with this reversible reaction permits real-time, direct measurement of DA concentration. Fast scan cyclic voltammetry (FSCV) performed at CFEs has been considered the gold standard for the in vivo measurement of phasic DA signaling events for decades (Robinson et al., 2003; Wightman et al., 1988). While FSCV is highly effective at measuring transient DA, the necessity for background subtraction of large capacitive currents has prevented the use of FSCV for the detection of resting DA concentrations. Microdialysis is widely used to observe resting DA in vivo (Auclair et al., 2002; Carboni et al., 1989; Carboni et al., 2001; Di Chiara et al., 1993; Pontieri et al., 1995; Rassoulpour et al., 2005; Wu et al., 2007). However, implantation of large microdialysis probes (~200 μm o.d.×1 mm) results in substantial tissue damage that greatly diminishes extraction efficiency and prevents chronic measurement beyond 5-10 days (Bassareo et al., 2015; Borland et al., 2005; Jaquins-Gerstl and Michael, 2009; Jaquins-Gerstl et al., 2011; Nesbitt et al., 2013; Nesbitt et al., 2015; Varner et al., 2016). In addition, microdialysis is not commonly used to directly quantify basal concentration, but rather percent changes from baseline (Auclair et al., 2002; Carboni et al., 1989; Carboni et al., 2001; Di Chiara et al., 1993; Pontieri et al., 1995; Rassoulpour et al., 2005; Wu et al., 2007). Recently, several electrochemical approaches have been developed to measure drug induced changes in tonic DA over several hours at CFEs. This was accomplished by utilizing both charge balancing (Oh et al., 2016) and controlled DA adsorption waveforms (Atcherley et al., 2015a; Atcherley et al., 2013; Atcherley et al., 2015b; Burrell et al., 2015). One such method, Fast Scan Controlled Adsorption Voltammetry was capable of estimating the basal DA concentration in mouse dorsal striatum (DS, ~90 nM) (Atcherley et al., 2015b) with a ~20 second temporal resolution.

This example illustrates dopamine detection methods using a probe with a conductive polymer coating comprising poly (3,4-ethylene dioxythiophene) doped with negatively charged carbon nanotubes (PEDOT/CNT). PEDOT/CNT can be controllably deposited onto both macro-(Xu et al., 2013) and microelectrodes (Alba et al., 2015; Kozai et al., 2016; Luo et al., 2011) via electropolymerization, resulting in increased effective surface area, increased charge storage capacity (increased capacitance) and decreased electrode impedance (Alba et al., 2015; Kozai et al., 2016; Luo et al., 2011; Xu et al., 2013). PEDOT/CNT coated microelectrodes have exhibited excellent in vivo performance for both electrophysiological recording (Alba et al., 2015; Kozai et al., 2016) and electrical stimulation (Luo et al., 2011) over several months of chronic implantation. Furthermore, PEDOT/CNT coated carbon paste macroelectrodes are highly sensitive and selective for the electrochemical detection of resting DA in vitro via differential pulse voltammetry (Xu et al., 2013). In this Example it is shown that the PEDOT/CNT coating on both implantable CFEs and gold electrode sites along a single shank silicon-based microelectrode array (MEA) produce a highly adaptable and robust new electrode technology capable of directly quantifying resting (tonic) DA in the rat DS with high spatial and temporal resolution.

Materials and Methods

Electrode Preparation

CFEs were produced using previously described methods (Taylor et al., 2013; Taylor et al., 2012; Taylor et al., 2015; Taylor et al., 2017b). Briefly, single 7 µm diameter carbon fibers (T650; Cytec Carbon Fibers LLC, Piedmont, S.C., USA) were aspirated into acetone filled borosilicate glass capillaries (0.4 mm ID, 0.6 mm OD; A-M systems Inc., Sequim, Wash., USA) until 1 cm of the fiber remained exposed out of each end. Acetone was removed via capillary action and the borosilicate glass was pulled into two fine tips (glass tapers to 8 µm OD) using a heated filament vertical capillary puller (Narishige puller, Los Angeles, Calif., USA) and the two ends were separated by cutting the attaching carbon fiber. Carbon fibers were anchored to the pulled capillary by filling the glass taper with low viscosity epoxy (Spurr Epoxy; Polysciences Inc., Warrington, Pa., USA). The remaining exposed fiber was trimmed to 400 µm length (Taylor et al., 2017b) and preconditioned with a 10 min soak in isopropanol prior to use (Bath et al., 2000). Electrical connection was established with the electrode via a drop of mercury and a nichrome hookup wire (annealed nichrome; Goodfellow, Oakdale, Pa., USA).

Silicon-based neural recording MEAs were obtained from Diagnostic Biochips (Glen Burnie, Md., USA). MEAs consisted of a single silicon shank (90 µm×15 µm×7 mm) with 16 individual 37 µm diameter gold electrode sites centered and equally spaced along the shank at 200 µm increments (3 mm total electrode spacing). Additional details regarding MEA fabrication are provided, e.g., in Taylor et al., 2017a.

PEDOT/CNT Coating

PEDOT/CNT functionalization was conducted using previously established methods (Alba et al., 2015; Kozai et al., 2016; Luo et al., 2011; Taylor et al., 2017b; Xu et al., 2013). 0.2 g of multiwall carbon nanotubes (MWCNTs, 10-20 nm diameter, 10-30 µm length, 95% purity, Nanostructured & Amorphous Materials Inc., Houston, Tex., USA) were functionalized to have a negative charge by first refluxing with 25 mL of pure nitric acid and 75 mL of pure sulfuric acid in a 1 L beaker for two hours while undergoing bath sonication at room temperature (FS110H Ultrasonic cleaner, Fisher Scientific, Pittsburgh, Pa., USA). The solution was then brought up to 35° C. and stirred overnight. Next, the solution was diluted to 1 L, the supernatant was poured off, the remaining solution was transferred into SnakeSkin dialysis membranes (3.5K MWCO, 35 mm diameter, Thermo Scientific, Rockford, Ill., USA) and placed in 4 L plastic bucket containing slowly stirred deionized water to neutralize pH. Dialysis water was pH tested and replaced every 6-12 hours until a neutral pH was obtained. To ensure that all acid had been removed from the MWCNTs, the membranes were transferred to a large crystallization dish filled with deionized water for an additional 2 hours of bath sonication and 6-12 hours of subsequent dialysis. The water/MWCNT solution was then transferred from the dialysis membrane to a round bottom flask and placed in a Rotovap to remove water. The resulting negatively charged CNTs were stored at −20° C. until use.

Polymerization solution was freshly prepared immediately prior to electrode polymerization by first dissolving 1 mg/mL of the negatively charged CNTs in nanopure water via bath sonication then adding 1 µL/mL of 3,4 ethylene dioxythiophene (EDOT, Sigma Adrich, St. Louis, Mo., USA). The solution was then vortexed prior to undergoing 45 minutes of pulsed probe sonication (2 seconds on, one second off, 20% power, 1.6 mm tip, Q500 Sonicator, QSonica LLC, Newtown, Conn., USA). Probe sonication aids in the dissolution of EDOT into the solution and serves to further break up the CNTs into smaller units (Du et al., 2018; Taylor et al., 2017b; Weaver et al., 2014). Following probe sonication, the solution was again vigorously mixed immediately prior to electropolymerization. Identical electropolymerization procedures were used for both CFEs and 37 µm diameter gold electrode sites located along single shank, silicon MEAs. Electrodes were polymerized via chronocoulometry using a 3-electrode design with either an individual CFE or an individual gold electrode located along the MEA as a working electrode, a platinum sheet counter electrode and a Ag/AgCl reference electrode. Chronocoulometry was performed at +0.9 V vs Ag/AgCl until reaching a final charge density of 100 mC/cm$^2$, upon which polymerization was terminated. Freshly polymerized electrodes were dip rinsed in water and stored dry at room temperature until use.

In Vitro Calibration

Electrochemical detection of resting DA was performed via square wave voltammetry (SWV). The SWV waveform was repeatedly applied from −0.2 V to 0.3 V at 25 Hz with a 50 mV pulse amplitude and a 5 mV step height every 15 seconds. Potential was held at 0 V between scans. In vitro DA calibration were performed using freshly prepared, nitrogen purged DA standard solutions dissolved in artificial cerebra spinal fluid (aCSF, 142 mM NaCl, 1.2 mM CaCl$_2$, 2.7 mM KCl, 1.0 mM MgCl$_2$, 2.0 mM NaH$_2$PO$_4$, pH 7.4). The sensitivity of both bare and PEDOT/CNT coated electrodes (CFE and MEA) for resting DA was determined by performing in vitro SWV calibration in aCSF, 100 nM DA, 250 nM DA, 500 nM DA and 1 µM DA. PEDOT/CNT coated CFEs were also calibrated using the above detailed procedure in the presence of 200 µM ascorbic acid (AA). Electrode sensitivity was determined by the linear slope of the calibration plot relating DA peak current to DA concentration. SWV selectivity for DA at PEDOT/CNT coated CFEs was determined by performing SWV measurements in individually prepared solutions of DA (1 µM), AA (200 µM), DOPAC (10 µM), uric acid (10 µM), hydrogen peroxide (200 µM), serotonin (1 µM) and norepinephrine (1 µM) (all chemicals obtained from Sigma Aldrich, St. Louis, Mo., USA). Selectivity was assessed via direct comparison of SWV peak potentials for each molecule.

In Vivo Procedure

Figure 9:
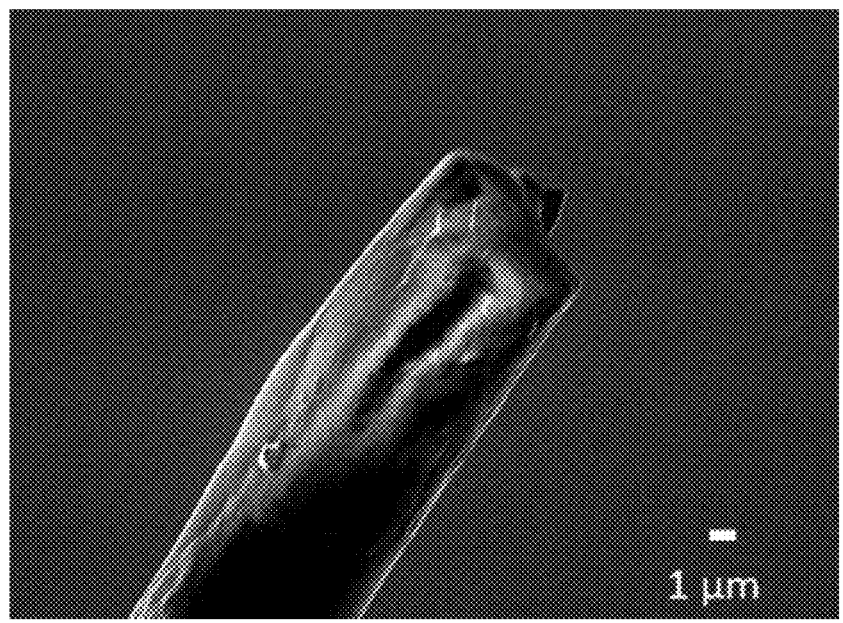
FIG. 9. SEM imaging displays that PEDOT/CNT functionalized CFEs become entirely encased with biological material upon in vivo explanation.

The in vivo performance of PEDOT/CNT coated CFEs was determined through acute surgical experiments conducted in anesthetized rats. All animal procedures were performed according to protocols approved by the University of Pittsburgh Institutional Animal Care and Use Committee. Individual male Sprague Dawley rats (350-450 g, Charles River, Wilmington, Mass., USA) were anesthetized with 2% isoflurane by volume (Henry Schein, Melville, N.Y., USA) and positioned in a stereotaxic head restraint to flat skull orientation. The skull and dura were removed to allow for the positioning of a single PEDOT/CNT coated CFE into the dorsal striatum (2.5 mm lateral and 0.42 mm anterior of bregma, 5 mm below the cortical surface) and two additional holes were bored into the skull to accommodate the positioning of a Ag/AgCl reference electrode contralaterally to the CFE and a bone screw counter electrode caudally to the reference. The SWV waveform (detailed above) was applied immediately upon finalizing electrode placement and was repeated over a 75-minute period. Following 30 minutes of data collection, rats were administered with either 20 mg/kg, i.p. nomifensine (Sigma Aldrich, St. Louis, Mo., USA) (Taylor et al., 2012) or saline vehicle. Upon reaching the predetermined experimental endpoint, the CFE was explanted for post calibration (using above detailed in vitro protocols) and the animal was humanly sacrificed using approved procedures. As illustrated at FIG. 9, SEM imaging displays that PEDOT/CNT coated CFEs become entirely encased with biological material upon in vivo explanation.

A single proof-of-principle in vivo experiment to investigate the performance of PEDOT/CNT coated MEAs was performed using the same surgical procedures detailed above. The only difference is that the PEDOT/CNT coated CFE was replaced with an MEA with three individual electrode sites coated with PEDOT/CNT spanning a 2.8 mm total vertical distance. The middle electrode was located 1.2 mm above the ventral-most electrode). The MEA was implanted into the DS (same medial-lateral and anterior-posterior coordinates as above) to a final depth of 5.4 mm below the cortical surface. This resulted in two PEDOT/CNT coated MEA electrode sites located in the S and one PEDOT/CNT coated electrode site located in the forelimb region of the primary somatosensory cortex. The SWV waveform was repeated performed at each of the three PEDOT/CNT coated electrodes in succession over a period of 75 minutes. 20 mg/kg, i.p. nomifensine was delivered after 30 minutes of data collection. Upon reaching the predetermined experimental endpoint, the MEA was removed for post calibration and the animal was humanely sacrificed.

In vivo DA concentration was determined for all in vivo experiments by converting SWV peak current to DA concentration using the post calibration electrode sensitivity.

Data Analysis

MATLAB (MathWorks Inc., Natick, Mass., USA) was used to perform all data analysis, IBM SPSS software (v22, IBM Corp, Armonk, N.Y., USA) was used to perform all statistical comparisons and Microsoft Excel and PowerPoint (Microsoft, Redmond, Wash., USA) were used to produce finalized figures. Each SWV response was first filtered using a zero-phase, forward and reverse (filtfilt) low-pass, $3^{rd}$ order Butterworth digital filter with the 3-dB cutoff at 0.25 normalized frequency units to remove electrochemical noise. The zero-phase, forward and reverse filter design was chosen to ensure that the SWV peak shape and position was not distorted by the lowpass filter. The DA peak was then isolated from the nonfaradaic background current for each SWV scan by subtracting the polynomial baseline, determined by fitting a $2^{nd}$ order polynomial to the SWV current values corresponding to the +0.05 V to 0.07 V and +0.26 V to 0.3 V potential regions located on either side of the DA peak. In vivo DA concentration versus time plots were filtered using a zero-phase, forward and reverse low-pass, $3^{rd}$ order Butterworth digital filter with the 3-dB cutoff at 0.1 normalized frequency units to remove high frequency noise.

Scanning Electron Microscopy

Individual bare CFEs and PEDOT/CNT coated CFEs were imaged using scanning electron microscopy at the University of Pittsburgh, Center for Biological Imaging using a JSM6330 scanning electron microscope (Jeol, Peabody, Mass., USA). The glass electrode tapers were broken off and mounted to the stage using conductive copper tape for grounding. 1000× magnification images were collected under vacuum using a 3 kV acceleration voltage and a working distance automatically adjusted for optimal image quality.

Results and Discussion

PEDOT/CNT Polymerization of CFEs

Isopropanol pretreated CFEs undergo successful PEDOT/CNT functionalization upon+0.9 V chronocoulometry electrodeposition with a 100 mC/cm$^2$ charge density cutoff. In a previous study chronopotentiometry was used to electropolymerize CFEs with a nanocomposite coating containing PEDOT and graphene oxide (Taylor et al., 2017b). While chronopotentiometry would have still been effective for PEDOT/CNT polymerization, in this Example, chronocoulometry paired with a fixed charge density cutoff to account for measured differences in CFE surface area was used. The surface area designated for the charge density cutoff was determined by measuring the length and radius of each individual CFE prior to polymerization. Due to the deep ridge morphology of CFE surfaces (FIG. 1B), these measurements are an underestimation of the actual surface area. All of the CFEs fabricated for this study were manufactured using the same stand of T650 carbon fiber. As such, the striation from CFE to CFE should be similar, thus the calculated cylindrical surface area should scale directly with the actual electrode surface area through a conversion factor accounting for the uniform striated morphology.

1000× scanning electron microscopy imaging of a representative bare CFE (FIG. 1B) as well as a PEDOT/CNT coated CFE (FIG. 1C) confirms that PEDOT/CNT deposits as a thin, uniform coating on the CFE surface. The "birdsnest" morphology inherent to PEDOT/CNT electropolymerization has been previously shown on both macro—(Xu et al., 2013) and microelectrodes (Alba et al., 2015; Kozai et al., 2016; Luo et al., 2011) accompanied by decreased electrode impedance, increased electrode surface area, increased electrode capacitance and increased overall negative charge on the electrode surface due to the incorporation of highly charged functionalized CNTs. As predicted, PEDOT/CNT significantly decreases the average overall electrode impedance from bare CFEs (FIG. 1D, n=5) as well as at each frequency below 100 kHz. In addition, PEDOT/CNT functionalization significantly increases the capacitance of the CFE (FIG. 1E, n=5). The average amplitude of the nonfaradaic charging current in response to a 1 V/s CV sweep significantly increased from 0.067±0.003 μA to 3.40±0.09 μA. The material characteristics of these electrodes are so reproducible that the SEM error bars are practically invisible in FIGS. 1D and 1E. This speaks directly to the high quality of CFE manufacturing and of the highly controlled nature of the chronocoulometry electrodeposition protocol used in this Example.

Figure 10:
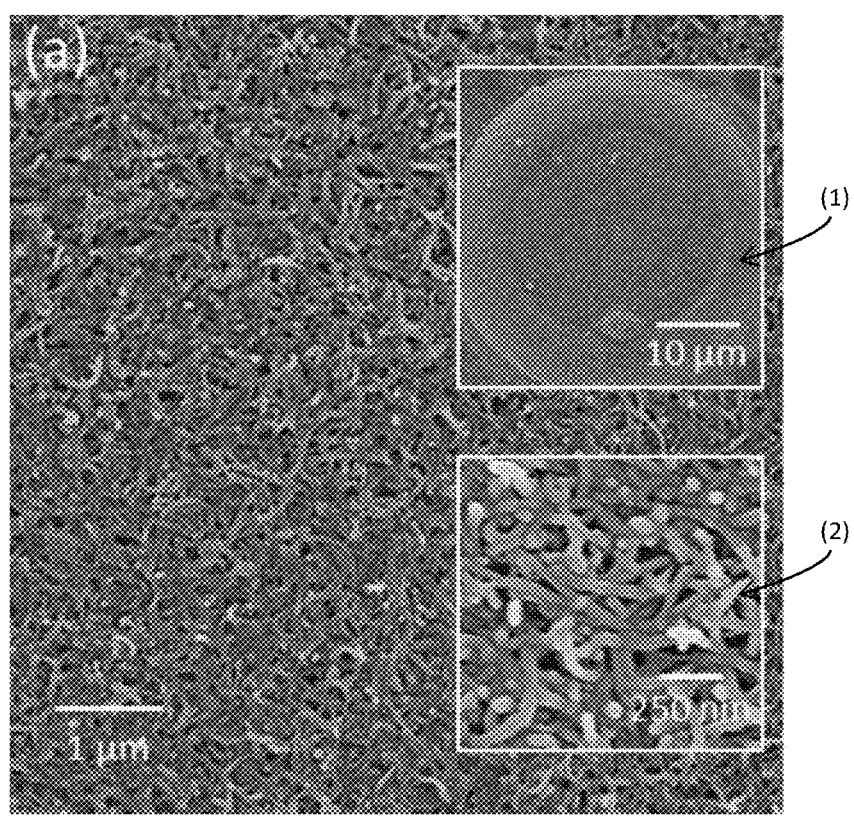
FIG. 10. SEM imaging displays that PEDOT/CNT selectively deposits onto the surface of individual 1200 µm² gold electrodes (inset, top, labeled (1)) located along silicon MEAs following 100 mC/cm² chronocoulometry electrodeposition. Individual carbon nanotubes intertwine to create a bird's nest morphology on the electrode surface (inset, bottom, labeled (2)).

As illustrated at FIG. 10 (top inset), the PEDOT/CNT coating selectively covers the entire electrode surface in a bird's nest morphology where individual carbon nanotubes can be easily resolved. As shown previously for CFEs, PEDOT/CNT coating results in a significant decrease in electrode impedance at frequencies below 100 kHz and an increase in capacitance as indicated by a significant increase in the amplitude of the non-faradaic charging current.

The increased electrode surface area, significantly decreased electrode impedance and significantly increased electrode capacitance following PEDOT/CNT polymerization indicate that PEDOT/CNT coated CFEs exhibit character more similar to a macroelectrode than a microelectrode. In essence, electropolymerization results in a carbon-based macroelectrode compressed into a microelectrode dimension of space. Electrochemistry is a surface phenomenon, as such, the sensitivity for the electrochemical detection of a given analyte increases with the overall electrode surface area. The goal of this Example was to develop a fully implantable microelectrode with extreme sensitivity and selectivity for DA such that the selective measurement of trace quantities of resting DA are possible within the complex brain environment. From a material characteristic standpoint, PEDOT/CNT coated CFEs appear to be an ideal candidate for such a sensor.

In Vitro Detection of Resting DA at PEDOT/CNT Coated CFEs

The performance of PEDOT/CNT coated CFEs as a sensor for the electrochemical detection of resting DA was determined via in vitro calibration experiments performed in aCSF. Xu et al. previously showed that PEDOT/CNT functionalized carbon paste macroelectrodes are sensitive and selective for resting DA over ascorbic acid (AA) interference using differential pulse voltammetry (Xu et al., 2013). Pulsed voltammetric methods, such as differential pulse voltammetry, are designed to directly measure resting analyte concentrations by isolating faradaic current resulting from redox activity derived from an electroactive analyte from non-faradaic charging currents resulting from the application of a potential waveform (Bard and Faulkner, 2001). In this study we update the methodology from that used by Xu et al. by incorporating square wave voltammetry (SWV), a pulse voltammetry technique that allows for the isolation of faradaic current with improved rate of collection and increased peak current amplitude as compared to differential pulse voltammetry (Bard and Faulkner, 2001; Osteryoung and Osteryoung, 1985; Ramaley and Krause, 1969).

The SWV potential waveform consists of a combination of a stair step (FIG. 2A) and a square wave (FIG. 2B) where the amplitude and direction, frequency of each feature as well as the potential limits are predetermined by the user prior to waveform application. The resulting SWV waveform (FIG. 2C) consists of a series of anodic and cathodic step and holds that transverse a predetermined potential window. The waveform ascent through the potential window is clearly shown by the markers labeled (2) denoting the midpoint of each square wave step in FIG. 2C. PEDOT/CNT coated CFEs are capable of measuring a 1 µM DA solution using a SWV waveform consisting of a +5 mV potential stair step (FIG. 2A) and a 50 mV square wave amplitude (FIG. 2B) scanned at a 25 Hz frequency (20 ms hold per step) from −0.2 V to +0.3 V. The SWV waveform was applied every 15 seconds, with a 0 V potential hold between scans to facilitate DA adsorption. Forward current (FIG. 2E) is sampled for each potential step at the end of the anodic hold portions of the waveform immediately prior to the subsequent cathodic step (FIG. 2C, labeled (1)) and the backward current (FIG. 2E) is sampled for each potential step at the end of the cathodic hold portions of the waveform immediately prior to the subsequent anodic step (FIG. 2C, labeled (3)). The final SWV current response (FIG. 2F) reflects the difference between the forward and backward current responses. The underlying theory inherent to pulse voltammetry is that capacitive currents decay proportional to $e^{-t}$ whereas faradic current decay more slowly proportional to $t^{-1/2}$ (Bard and Faulkner, 2001). Current sampling at the end of the hold period allows for a more selective measurement of faradic currents by allowing the nonfaradaic capacitive currents to dissipate to a greater degree prior to current measurement.

FIG. 2D illustrates the chemical changes to DA that result in measurable current. SWV measurement of 1 µM DA reveals a clear faradaic peak resulting from the oxidation of DA to dopamine-o-quinone (DAoQ) in the forward scan (FIG. 2E) whereas the backward scan shows a clear faradaic peak resulting from the reduction of DAoQ back to DA (FIG. 2E). Subtraction of the forward and backward current responses reveals a single current peak for DA and has the overall effect of amplifying the total faradic peak current while removing latent capacitive current features (FIG. 2F).

The performance of PEDOT/CNT coated CFEs for the electrochemical detection of resting DA was further examined by expanding in vitro calibration protocols to include varying DA concentrations and common neurochemical interferents. Five individual electrodes were subjected to SWV measurement, first in aCSF and then in solutions of increasing DA concentration designed to encompass the expected in vivo DA concentration range (100 nM, 250 nM, 500 nM, 1000 nM). PEDOT/CNT coated CFEs exhibit clear, robust detection of resting DA at each concentration with the average SWV traces (SEM removed for clarity) revealing a single concentration dependent peak located near 0.18 V (FIG. 3A).

Figure 3C:
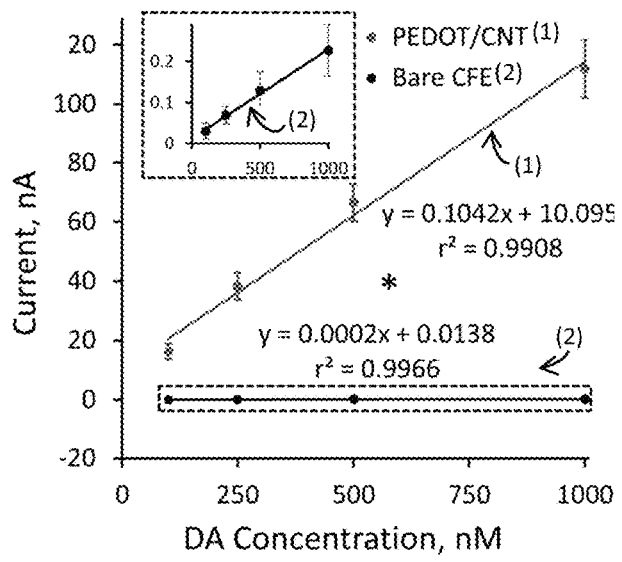

The average responses (±SEM) for each DA concentration following aCSF subtraction (FIG. 3B) reveals clear gaussian peaks as predicted by theory (Bard and Faulkner, 2001; Osteryoung and Osteryoung, 1985; Ramaley and Krause, 1969). Electrode sensitivity for the electrochemical detection of resting DA was defined as the linear slope of the calibration plot relating SWV peak current to DA standard concentration. The average DA calibration plot for PEDOT/CNT coated CFEs (FIG. 3C, markers labeled (1), n=5) is highly linear ($r^2$>0.99) with a 0.104±0.009 nA/nM sensitivity for resting DA detection. Average SWV DA detection at bare CFEs is also highly linear (FIG. 3C, markers labeled (2): see insert, n=3) but exhibits only a 0.000086±0.000062 nA/nM sensitivity. Direct comparison of DA sensitivity at bare and PEDOT/CNT coated CFEs reveals that PEDOT/CNT significantly increases electrode sensitivity for DA by 520-fold (one-way ANOVA, p<0.05). These results unequivocally confirm the effectiveness of SWV measurement at PEDOT/CNT coated CFEs for the direct detection of resting DA. In addition, this technology represents the first ever CFE/SWV-based sensing modality for the direct measurement of resting DA. PEDOT/CNT facilitates DA detection primarily via two mechanisms. 1) PEDOT/CNT deposits as a high surface area "birds-nest" morphology (FIG. 1C). Electrochemistry is a surface phenomenon. Increasing electrode surface area increases the amount of contact that the electrode can make with the surrounding solution, and thus the analyte of interest (DA). Increased contact with DA results in more redox activity and higher currents. 2) PEDOT/CNT carries a net negative charge due the incorporation of acid functionalized CNTs. DA is positively charged at physiological pH (7.4). Incorporation of a negatively charged nanocomposite surface will facilitate DA adsorption (Taylor et al., 2017b).

Figure 3D:
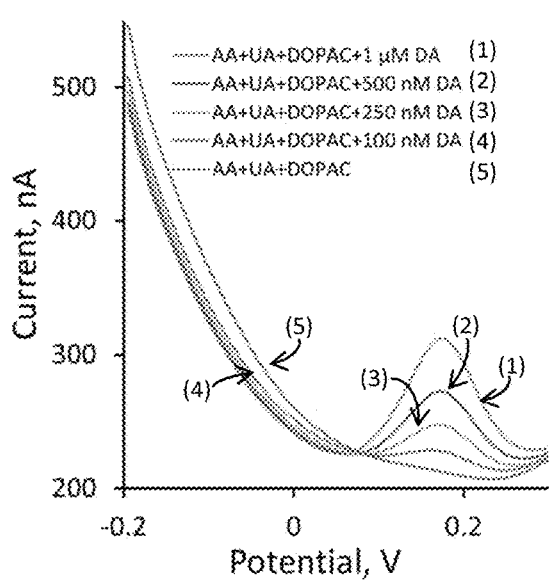

It is preferred that SWV detection be selective over common neurochemical interferents found throughout the complex brain environment. To assess selectivity, DA calibrations were performed at PEDOT/CNT functionalized CFEs in aCSF containing a cocktail of common neurochemical interferents prepared to reflect expected physiological concentrations in the rat dorsal striatum. The interferent cocktail consisted of 200 µM AA, 10 µM uric acid (UA) and 10 µM DOPAC pH adjusted to 7.4. The average (n=5, SEM removed for clarity) baseline SWV response in the presence of the contaminant cocktail (FIG. 3D, line 5) showed an overall increase in the background current (as compared to aCSF alone, FIG. 3A, line 5) but no apparent faradaic current peaks within the −0.2 V to 0.3 V potential window. Introduction of increasing concentrations of DA results in the formation of a clear faradaic peak located at 0.18 V (FIG. 3D). This peak location is in complete agreement with calibrations performed in aCSF alone (FIG. 3A).

Figure 3E:
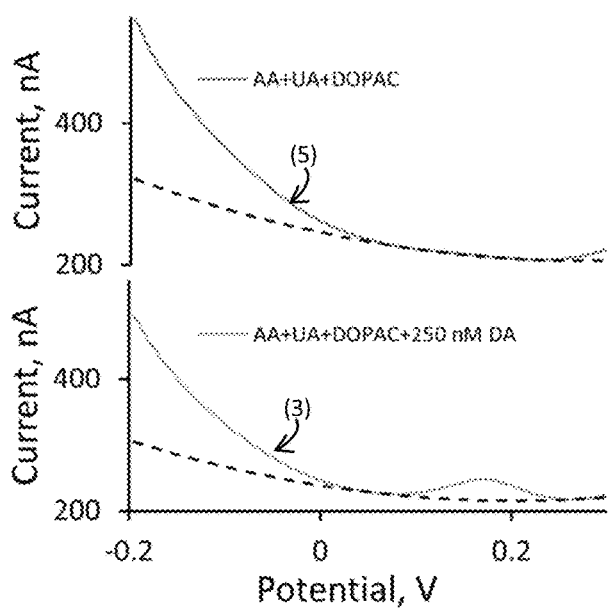
Figure 3F:
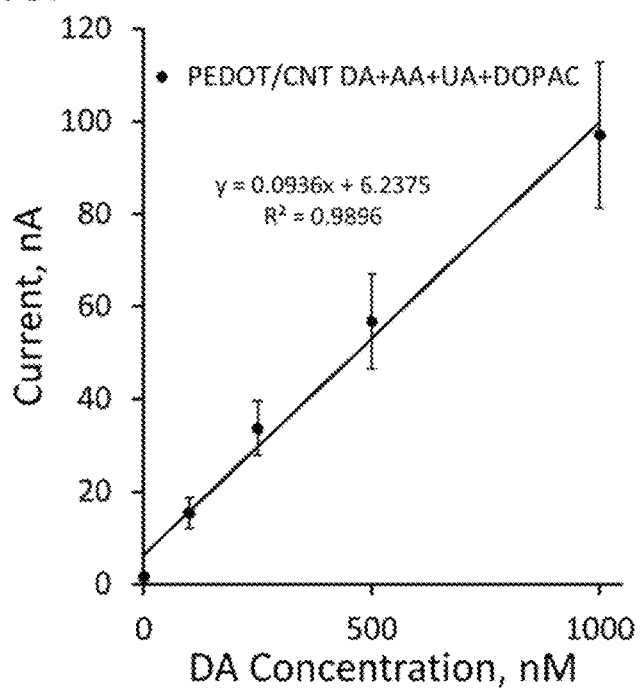

The faradaic DA peak can again be isolated using the previously described polynomial background subtraction procedure. The effectiveness of the $2^{nd}$ order polynomial fit for modelling the SWV baseline current response within the potential region of interest (+0.1 V to +0.25 V) in the presence of the AA, UA, DOPAC interferent cocktail is displayed by modelling the average SWV current responses (shown in FIG. 3D) for AA, UA and DOPAC alone (FIG. 3E, line 5) and AA, UA, DOPAC+250 nM DA (FIG. 3E, line 3). The $2^{nd}$ order polynomial produces a highly correlation fit over the +0.1 V to +0.25 V potential region of interest to the average SWV current response collected in the interferent cocktail alone (FIG. 3E, top dashed line) and also draws a suitable nonlinear baseline under the DA peak for the AA, UA, DOPAC+250 nM DA average SWV response (FIG. 3E, bottom dashed line). The subtraction of the polynomial derived baseline from the raw SWV response results in a clear Gaussian shaped peak centered around 0.18 V for DA containing standards and no discernable peak for the interferent cocktail alone. The average (±SEM) DA calibration plot for PEDOT/CNT functionalized CFEs following polynomial background subtraction in the presence of the AA, UA, DOPAC interferent cocktail (FIG. 3F, n=5) is highly linear with a 93±15 nA/µM sensitivity for resting DA detection. This sensitivity is not significantly different than the sensitivity obtained by DA calibration in aCSF alone. This indicates that the combined usage of PEDOT/CNT functionalized electrodes, SWV detection and polynomial baseline subtraction allows for the sensitive and selective detection of DA.

It is notable that PEDOT/CNT coated CFEs provide such excellent selectivity over such a range of neurochemical interferents, most notably DOPAC and AA. DOPAC and AA have similar standard reduction potentials to DA (Schmidt et al., 2013) and are present in the brain at concentrations that are orders of magnitude higher than DA (Smith et al., 1992; Venton et al., 2002). As such, electrochemical measurement of sub-micromolar DA concentrations in the presence of DOPAC and AA has proven challenging. PEDOT/CNT owes its excellent selectivity over DOPAC and AA to electrostatic repulsion (Xu et al., 2013). As previously mentioned, PEDOT/CNT nanocomposite coatings are negatively charged due incorporation of highly charged functionalized CNTs. DOPAC and AA also carry a negative charge at physiological pH (7.4). Electrostatic repulsion prevents DOPAC, AA and any other negatively charged interferent molecule from approaching the electrode surface and contributing to the SWV current. This only further illustrates how critical the PEDOT/CNT nanocomposite coating is to resting DA detection.

Polynomial Baseline Subtraction for Self-Contained DA Measurement

FSCV is a well-established electrochemical method for real-time in vivo DA measurement. While FSCV is highly effective at measuring sub second phasic DA changes, it is unable to quantify resting DA. Application of the FSCV waveform produces a large nonfaradaic capacitive charging current that must be removed to quantify faradaic current. In addition, the background signal designated for subtraction must be constantly refreshed to account for effects relating to electrochemical drift. When performing in vivo FSCV, the background signal designated for subtraction is collected directly from the tissue being studied. Subtraction of an in vivo background signal not only removes current inherent to the nonfaradaic charging current, but also removes any current inherent to the basal concentration of electroactive analytes.

For accurate quantification of basal DA, it is preferred for the methodology to not rely on periodic in vivo background subtraction. This example provides a highly effective method for establishing a rolling SWV baseline based on $2^{nd}$ order polynomial fitting that can be used to selectively isolate current that is DA in origin. This allows for each SWV scan to be considered as a stand-alone entity for the purpose of converting peak current to DA concentration.

Figure 4A:
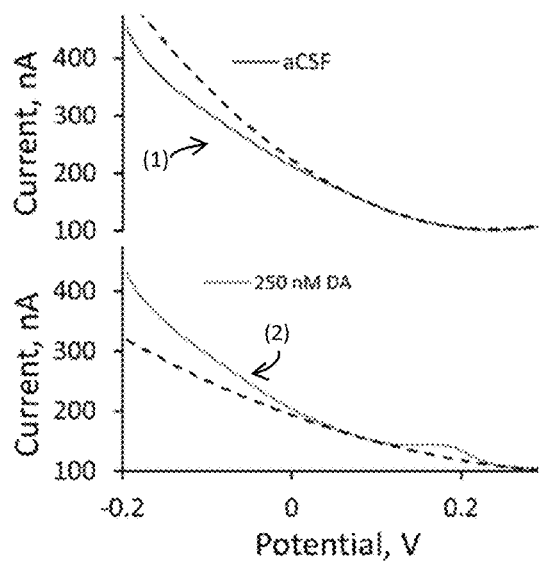
FIGS. 4A-4C. Polynomial background modeling.

The majority of the DA gaussian current peak is located between +0.1 V and +0.25 V (FIG. 3B). As a consequence, current corresponding to all other potential regions is of little interest for DA quantification. DA peak isolation presents a challenge in that the baseline SWV current over the +0.1 V to +0.25 V potential region of interest is nonlinear (FIG. 4A, plot labeled (1)). Therefore, simply drawing a straight baseline over the potential region of interest for peak isolation results in an underestimation of peak height. Accurate isolation of the DA peak is facilitated by knowledge of the nonlinear baseline SWV response. It is shown herein that the baseline SWV current response over the +0.1 V to +0.25 V potential region of interest can be easily fit using a $2^{nd}$ order polynomial. The fit only requires the input of a few current values above (0.26 V to 0.3 V) and below (+0.05 V to +0.07 V) the potential window of interest. The resulting fit equation can then be extrapolated to encompass the entire potential window and serve as a self-contained baseline subtraction for DA peak isolation. The upper and lower current input bounds for the $2^{nd}$ order polynomial are determined using an iterative peak localization algorithm described in the methods section.

The fit for the polynomial baseline was determined using a two-step peak extraction method consisting of an iterative peak localization algorithm. First, a linear baseline was initialized with two signal points on either side of a user-selected DA peak maximum voltage (0.18 V for DA). Signal points used to construct the baseline were iteratively updated to produce a final baseline which maximized the subtracted peak amplitude. The resulting linear fit intersects boundary points at either side of the DA peak profile. Portions of the SWV signal existing outside of these bounds closely approximate signals obtained in the absence of DA. The five data points located immediately adjacent to the upper and lower bounds were then modelled using a $2^{nd}$ order polynomial fit. This polynomial fit was extrapolated over the entire SWV potential window and subtracted from the raw SWV response for the purpose of peak extraction.

The effectiveness of the $2^{nd}$ order polynomial fit for modelling the SWV baseline current response within the potential region of interest (+0.1 V to +0.25 V) is clearly displayed by modelling the average SWV current responses (previously presented in FIG. 3A) for aCSF (FIG. 4A, line 1) and 250 nM DA (FIG. 4A, line 2). The $2^{nd}$ order polynomial produces a calculated baseline that is almost identical over the +0.1 V to +0.25 V potential region of interest to the raw SWV current response collected in aCSF (FIG. 4A, top dashed line). The $2^{nd}$ order polynomial remains functional following the introduction of 250 nM DA (FIG. 4A, bottom dashed line), drawing an adequate non-linear baseline below the DA peak centered at 0.18 V. The average SWV responses (±SEM) for each DA concentration following polynomial subtraction (FIG. 4B) reveals clear Gaussian peaks as predicted by theory. This Gaussian peak shape serves as evidence supporting the use of a polynomial baseline subtraction method for faradaic DA peak isolation. Further validation supporting the use of this polynomial baseline subtraction method was provided through the comparison of DA calibration plots.

Figure 4B:
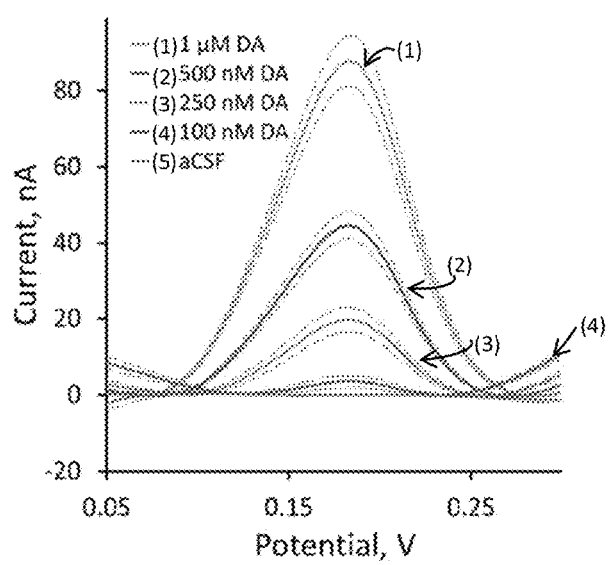
Figure 4C:
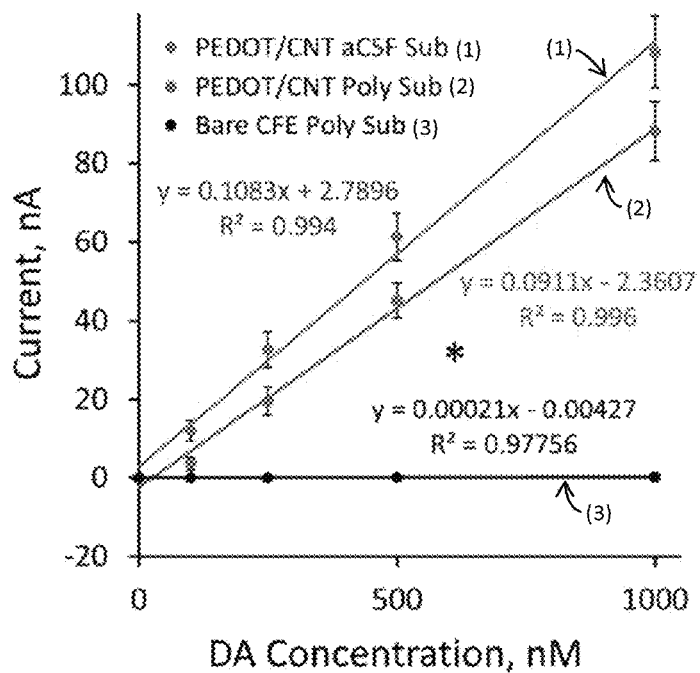

Electrode sensitivity for the electrochemical detection of resting DA was defined as the linear slope of the calibration plot relating the background subtracted SWV peak current to DA standard concentration. The average (±SEM) DA calibration plot, generated by plotting the average maximum peak current from five individual PEDOT/CNT functionalized CFEs following polynomial background subtraction (FIG. 4C, line 2, n=5) is highly linear ($r^2$>0.99) with a 90.±7 nA/µM sensitivity for resting DA detection. The average (±SEM) calibration plot for bare CFEs following polynomial background subtraction is also highly linear (FIG. 4C, line 3, n=3) but exhibits only a 0.21±0.08 nA/µM sensitivity. The average sensitivities reported were determined by averaging the individual sensitivities for each separate electrode. The linear regression fit on the average calibration plot (FIG. 4C) is presented for the purpose of illustrating average sensitivity, not to quantify average sensitivity. This explains the slight deviation from the reported average sensitivity and the slope produced by the average calibration plot (FIG. 4C). Direct comparison of DA sensitivity at bare and PEDOT/CNT functionalized CFEs reveals that PEDOT/CNT significantly increases electrode sensitivity for DA by 422-fold (one-way ANOVA, p<0.05). These results unequivocally confirm the effectiveness of SWV measurement at PEDOT/CNT functionalized CFEs for the direct detection of resting DA. The relatively poor performance of bare CFEs for the in vitro detection of resting DA using SWV as compared to previous studies using DNPV can be clearly explained by differences in electrode preparation. Studies using DNPV employed CFEs composed of a larger exposed carbon fiber (12 µm diameter, 700 µm length) that had undergone extensive electrochemical pretreatment (2.8 V max voltage) to increase electrode sensitivity.

Validation of the $2^{nd}$ order polynomial baseline subtraction method for isolating the faradaic DA peak current was performed by comparing the previously described average (±SEM) PEDOT/CNT calibration plot constructed following polynomial baseline subtraction (FIG. 4C, line 2) to the average (±SEM) calibration plot constructed from the same PEDOT/CNT functionalized CFEs following traditional aCSF baseline subtraction (FIG. 4C, line 1). The average calibration response for DA following aCSF subtraction is highly linear ($r^2$>0.99) with a 108±9 nA/µM sensitivity for resting DA detection. The average sensitivity for DA detection obtained by aCSF background subtraction is not significantly different from the 90±7 nA/µM sensitivity for resting DA detection obtained using the previously described polynomial background subtraction method (one-way ANOVA, p>0.05). Although not significant, it should be noted that the DA peaks obtained by polynomial background subtraction exhibit slightly smaller peak heights than aCSF subtraction. The average sensitivity for DA following polynomial subtraction is 83% of the sensitivity produced by aCSF subtraction. This indicates that the $2^{nd}$ order polynomial fit modelled in the presence of 250 nM DA is slightly shallower than for true baseline exhibited by aCSF alone. Regardless of the 17% signal loss, the polynomial baseline subtraction method produces clear, quantifiable Gaussian peaks for the electrochemical detection of resting DA. It should also be noted that the signal loss associated with incorporating polynomial baseline subtraction will not introduce additional error into the quantification as long as it is used at each step of the experimental process (in vivo collection, in vitro calibration, etc.). The same ~17% error will be propagated at each step of the process.

SWV detection at PEDOT/CNT functionalized CFEs exhibit higher sensitivity for resting DA than FSCAV (81±11 nA/µM, Atcherley et al., 2013), charged balanced waveform FSCV (85.4±14.3 nA/µM$^{32}$) or convolution-based FSCV nonfaradiaic current removal (10.7±0.3 nA/Johnson et al., 2018). The sensitivity of electrochemically pretreated CFEs for resting DA using DNPV is not clearly defined in the literature. The average lower limit of detection for DA using PEDOT/CNT functionalized CFEs, defined at 3 times the standard deviation of the noise, was determined to be 2.03±0.09 nM, which is far below in vivo basal DA concentrations reported by Heien and Wightman (40-100 nM) (Atcherley et al., 2015b, Johnson et al., 2018).

It is important to note that the PEDOT/CNT nanocomposite coating facilitates successful DA detection. PEDOT/CNT deposits as a high surface area carbon-based "birds-nest" morphology (FIG. 1C). Acid functionalized CNTs are negatively charged, whereas DA is positively charged at physiological pH (7.4). Incorporation of negatively charged components onto the surface of the electrode will facilitate DA adsorption. Since electrochemistry is a surface phenomenon, increasing the electrode surface area with a material capable of selectively facilitating DA adsorption will increase sensitivity by concentrating DA onto the electrode surface. It should be noted that bare CFEs also exhibit a negatively charged surface due to the presence of oxygen containing functional groups but still exhibit poor sensitivity for resting DA via SWV detection (FIG. 4B). This suggests that the PEDOT/CNT mediated increase in sensitivity requires both an increase in negative charge and effective surface area.

Due to the highly porous and adsorptive nature of PEDOT/CNT coatings there is a concern that DA diffusion in-and-out of the coating will be restricted such that the temporal response of the electrode will be slowed and DA may actually become trapped within the coating. This concern has been alleviated by incorporating an 11 second 0 V (vs Ag/AgCl) hold into the SWV waveform. DA is able to diffuse 123 µm during the 11 second hold period ($\sqrt{2Dt}$, where D=6.9 cm$^2$/s). This time is more than sufficient for DA within the approximately 1.5 µm thick PEDOT/CNT coating to reach equilibrium with the surrounding environment. In addition, 0 V vs Ag/AgCl is a potential where DAoQ is reduced back to DA at physiological pH. This ensures that DA located within and directly surrounding the electrode coating is reduced prior to subsequent detection. The presence of retained DA within the PEDOT/CNT coating is not likely to affect the ability of PEDOT/CNT functionalized CFEs to accurately quantify in vivo basal DA, as the same retention would occur in both in vivo and in vitro settings. As such, any signal enhancement due to the retention of DA within the PEDOT/CNT coating will be reflected in the in vitro calibration. Incorporation of the 11 second hold into the SWV waveform results in an overall temporal resolution of 15 seconds for the detection of resting DA.

In Vivo Measurement of Basal DA at PEDOT/CNT Coated CFEs

Figure 5:
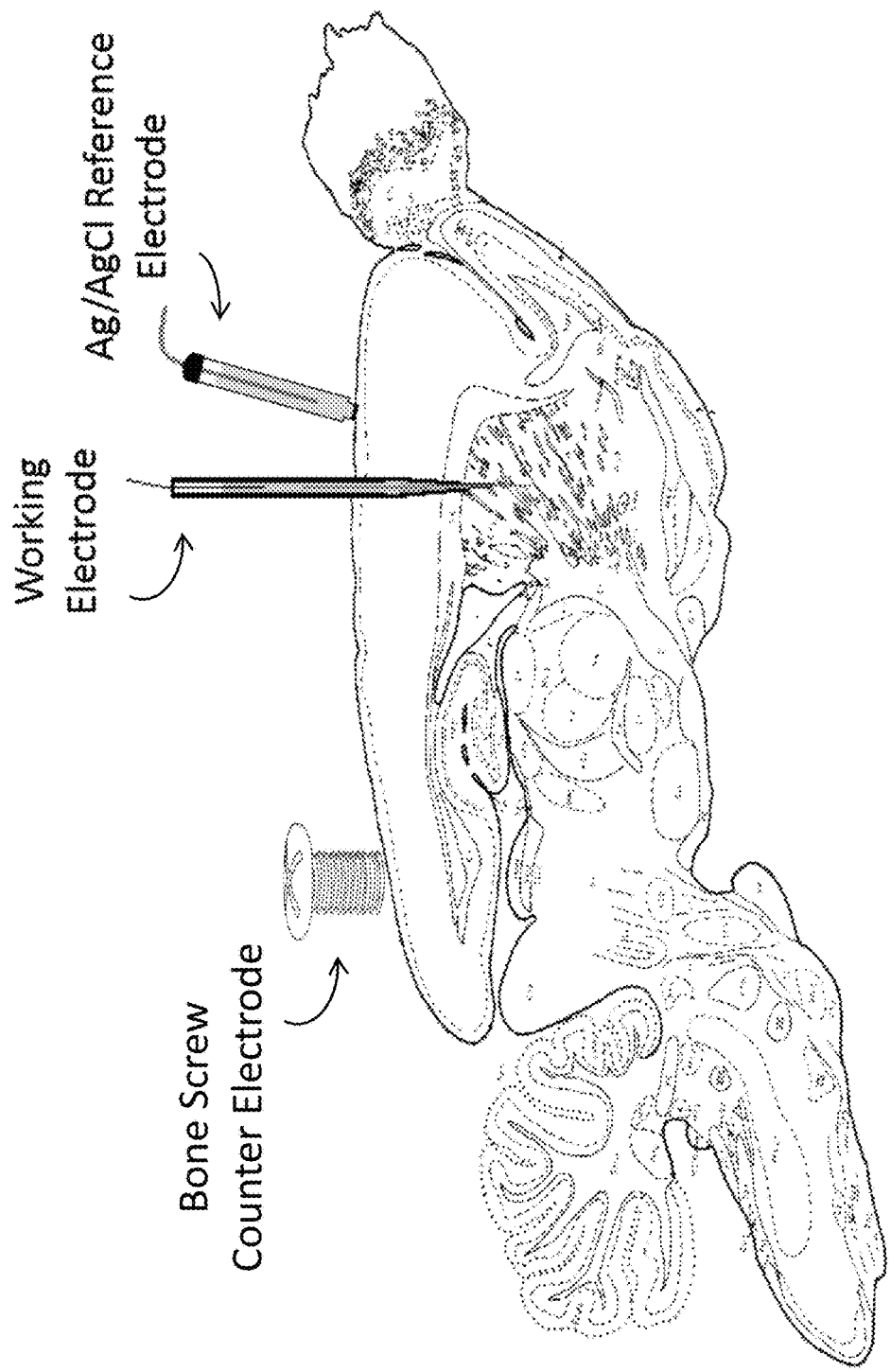
FIG. 5. Illustration of exemplary recording set up for DA detection in rat brain.
Figure 6A:
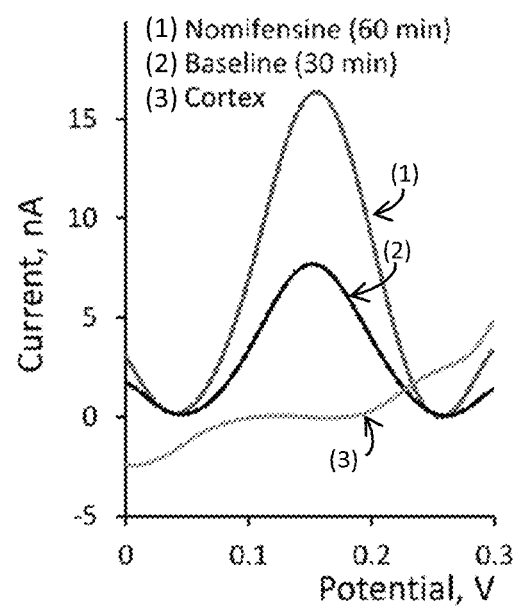
FIGS. 6A and 6B. PEDOT/CNT functionalized CFEs are capable of directly measuring basal DA in vivo.

The in vivo performance of the PEDOT/CNT coated CFEs for the detection of basal DA was determined through direct implantation into the DS of isoflurane anesthetized rats. In vivo data were collected using a 3-electrode design with a single PEDOT/CNT coated CFE working electrode lowered into the DS (2.5 mm lateral and 0.43 mm anterior to bregma, 5 mm below the cortical surface), a Ag/AgCl reference electrode placed contralaterally in contact with the meninges and a bone screw counter electrode positioned caudally to the reference (see FIG. 5). The SWV waveform (as discussed above) was applied immediately upon finalizing electrode placement and continuously repeated over a period of 90 minutes. Following 30 minutes of baseline SWV collection, n=3 individual rats received a single 20 mg/kg, i.p. injection of the competitive dopamine transporter inhibitor, nomifensine and n=3 individual rats received a single i.p. saline injection (vehicle). Nomifensine has previously been shown to increase basal DA. Application of the SWV waveform (accompanied by polynomial baseline subtraction) produced a clear DA peak (FIG. 6A, plot labeled (2)) which was increased following 20 mg/kg i.p. nomifensine (FIG. 6A, plot labeled (1)). The average (n=3, polynomial baseline subtracted) SWV response collected in the non-DA-rich forelimb region of the primary somatosensory cortex (S1FL, FIG. 6A) does not exhibit a discernable peak in the potential region of interest for DA. This clear absence of a DA peak in the non-DA containing S1FL provides clear support that the SWV peak recorded in the dorsal striatum is DA in origin. In vivo SWV peak current was converted to DA concentration using preimplantation in vitro electrode calibration. Preimplantation in vitro electrode calibration was chosen for the conversion of in vivo SWV current to DA concentration due to the observed stability of the in vivo current response. This stability is clearly evident in the lack of drift observed at PEDOT/CNT coated CFEs during saline controls (FIG. 6). Stability is observed immediately upon probe implantation (less than one minute) without requiring electrochemical in vivo stabilization. Post-explanation in vitro calibration was not used for the assignment of in vivo DA concentration due to a 71% decrease in in vitro DA sensitivity observed following probe explanation. This decrease in sensitivity is likely due to the encapsulation of the PEDOT/CNT coated CFE with biological matter (blood) during the explanation process (FIG. 9). This encapsulation is unlikely to occur during implantation as careful surgical technique was employed to ensure that implantation sites were free of blood. Additionally, encapsulation is unlikely during the 90 minutes of implantation because the acute timeframe is shorter than the time required for glial encapsulation (Kozai et al., 2015).

The average basal DA concentration in the dorsal striatum was quantified to be 82±6 nM (FIG. 4B, n=6). DA concentration in the dorsal striatum is comparable to measurements obtained in the nucleus accumbens of mice (90±9 nM) and rats (41±13 nM) by FSCAV, convolution-based FSCV respectively (Atcherley et al., 2015b). This measurement is also comparable to the 120±18 nM basal concentration reported in the rat striatum using m-CSWV (Oh et al., 2018) but an order of magnitude less than the measurement provided by FSCV experiments involving intracranial infusion of kynurenate (>2.6 µM) (Borland and Michael, 2004) and much higher than the 26±8 nM concentration obtained using DNPV in pargyline pretreated striatum. The immediate stability of the SWV peak current (FIG. 6) indicates that CFE implantation does not result in locally stimulated DA release. This is in agreement with other studies where basal DA was determined at acutely implanted CFEs.

Figure 6B:
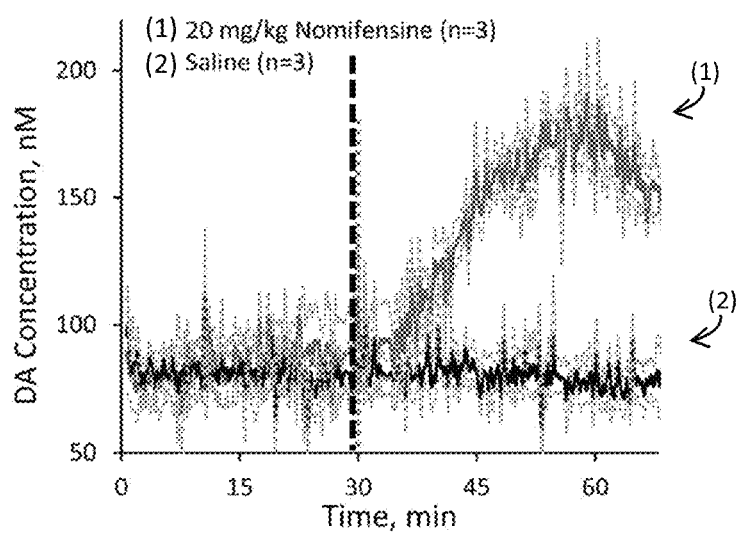

Following nomifensine injection at t=30 minutes, basal DA began to increase after approximately 5 minutes and continued to increase until reaching a maximum DA concentration 207±16 nM at 28±2 minutes following injection (FIG. 6B, plot labeled (1), n=3). The average DA response in saline control animals remained steady following i.p. injection (FIG. 6B, black, n=3). This nomifensine induced DA increase is in complete agreement with previous measurements of tonic DA using both electrochemistry 32 and microdialysis (Gu et al., 2015). We recognize the disparity in basal DA concentration reported by different techniques. At this point, it is difficult to know which estimate is correct, though it is notable that the change in basal DA induced by i.p. nomifensine injection is similar for each method, which adds legitimacy to each reported method. We are confident in our reproducibly measured 82±6 nM basal DA concentration due to the presence of a clear, nomifensine dependent DA peak observed during all in vivo measurements (FIG. 6A).

These findings show the effectiveness of performing SWV at PEDOT/CNT coated CFEs for the direct in vivo measurement of basal DA. In addition, this represents the first ever study to use SWV to measure in vivo DA concentration in a living animal.

DA Detection at PEDOT/CNT Coated MEAs

It is shown herein that PEDOT/CNT coated CFEs are sensitive and selective for the electrochemical detection of resting DA via SWV both in vitro and in vivo. In addition, it is established that incorporation of the PEDOT/CNT nanocomposite coating facilitates that detection. One of the most attractive features of conductive polymers is that they can be deposited onto a wide variety of conductive substrates. As electrochemistry is a surface phenomenon, it is reasonable to believe that this basal DA detection methodology can be transferred to another electrode substrate by selectively depositing the PEDOT/CNT nanocomposite coating. Silicon based MEAs developed for electrophysiological recordings are capable of measuring neural activity from multiple sites across different depths and widths of brain tissue with high-quality, single cell resolution (Obien et al., 2015). However, MEAs are not as widely used for neurochemical sensing because conventional electrode site materials (Au, Pt, Jr) are not sensitive and selective for electrochemical detection (Johnson et al., 2008) without substantial electrode modification (Lourenco et al., 2016; Rutherford et al., 2007; Tseng and Monbouquette, 2012; Vasylieva et al., 2015). Here the aim was to convert individual 1200 µm$^2$ gold electrode sites along a silicon MEA into functional basal DA sensing electrodes.

Figure 7C:
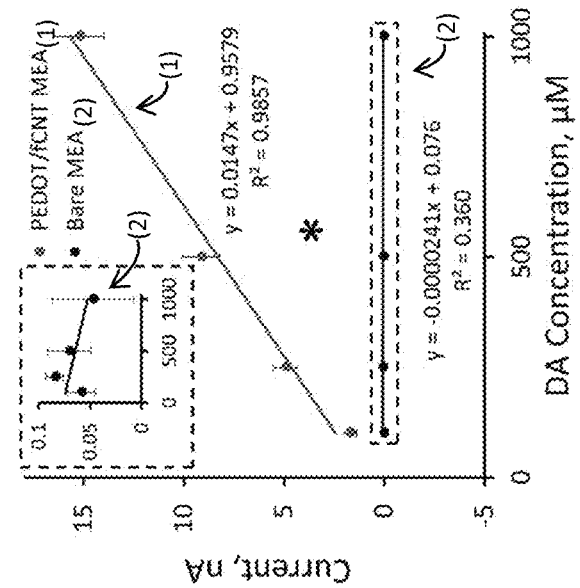
FIGS. 7A-7C. PEDOT/CNT functionalized MEAs are sensitive for resting DA in vitro.
Figure 7B:
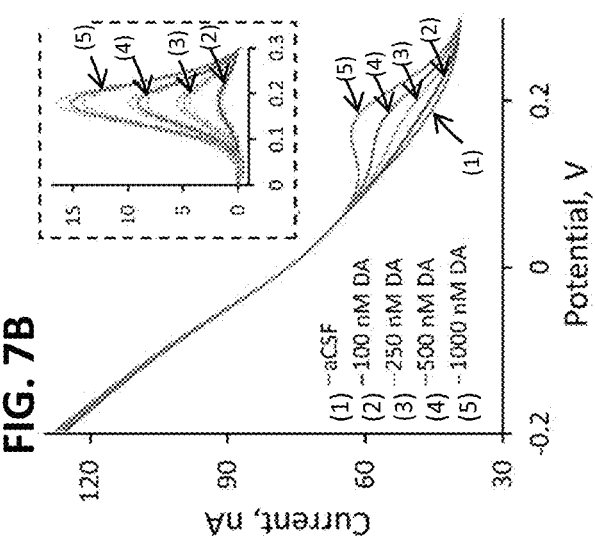
Figure 7A:
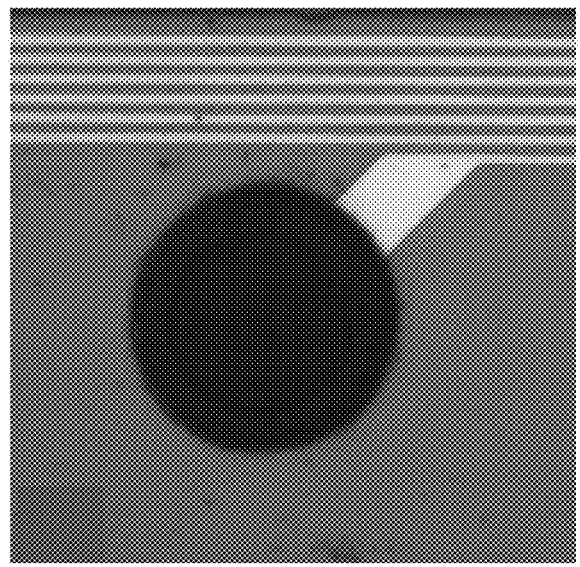

PEDOT/CNT coated MEAs perform in a strikingly similar manner to PEDOT/CNT coated CFEs. Individual gold electrode sites undergo selective, uniform PEDOT/CNT coating upon+0.9 V chronocoulometry electropolymerization with a 100 mC/cm$^2$ charge density cutoff (FIG. 7A). This results in a significant decrease in electrode impedance at frequencies below 100 kHz and an increase in capacitance as indicated by a significant increase in the amplitude of the nonfaradaic charging current. The average (n=5) in vitro DA calibration response at PEDOT/CNT coated MEAs produces a clear, concentration dependent gaussian DA peak (FIG. 7B, inset) centered around +0.18 V superimposed onto the baseline SWV current response (FIG. 7B). Comparison of the average peak current to DA concentration reveals excellent linearity and a 0.0147±0.0005 nA/μM average sensitivity (FIG. 7C). The sensitivity of PEDOT/CNT coated MEAs for resting DA detection is approximately 10× smaller than PEDOT/CNT coated CFEs. This is likely due to the approximately 10× difference in surface area present between the two electrode substrates prior to PEDOT/CNT coating. Incorporation of PEDOT/CNT onto the electrode surface is dramatically improved DA detection. In fact, bare gold MEA electrode sites are completely insensitive for DA detection via SWV (FIG. 7C, insert). On average (n=5), gold MEA electrodes do not display a concentration dependent SWV peak upon increasing DA concentration. This is apparent by the appearance of nonlinear, negative −0.000024±0.000029 nA/μM relationship between current and DA concentration. The ability to convert a totally DA-insensitive electrode substrate into a highly sensitive DA sensing electrode unequivocally reveals the power and versatility of PEDOT/CNT nanocomposite coatings. These findings suggest that any conductive substrate, whether inherently sensitive for the electrochemical detection of DA (i.e. CFEs) or not (i.e. gold MEA electrodes) can be converted into DA sensing electrodes by simply depositing a thin coating of PEDOT/CNT.

Figure 8:
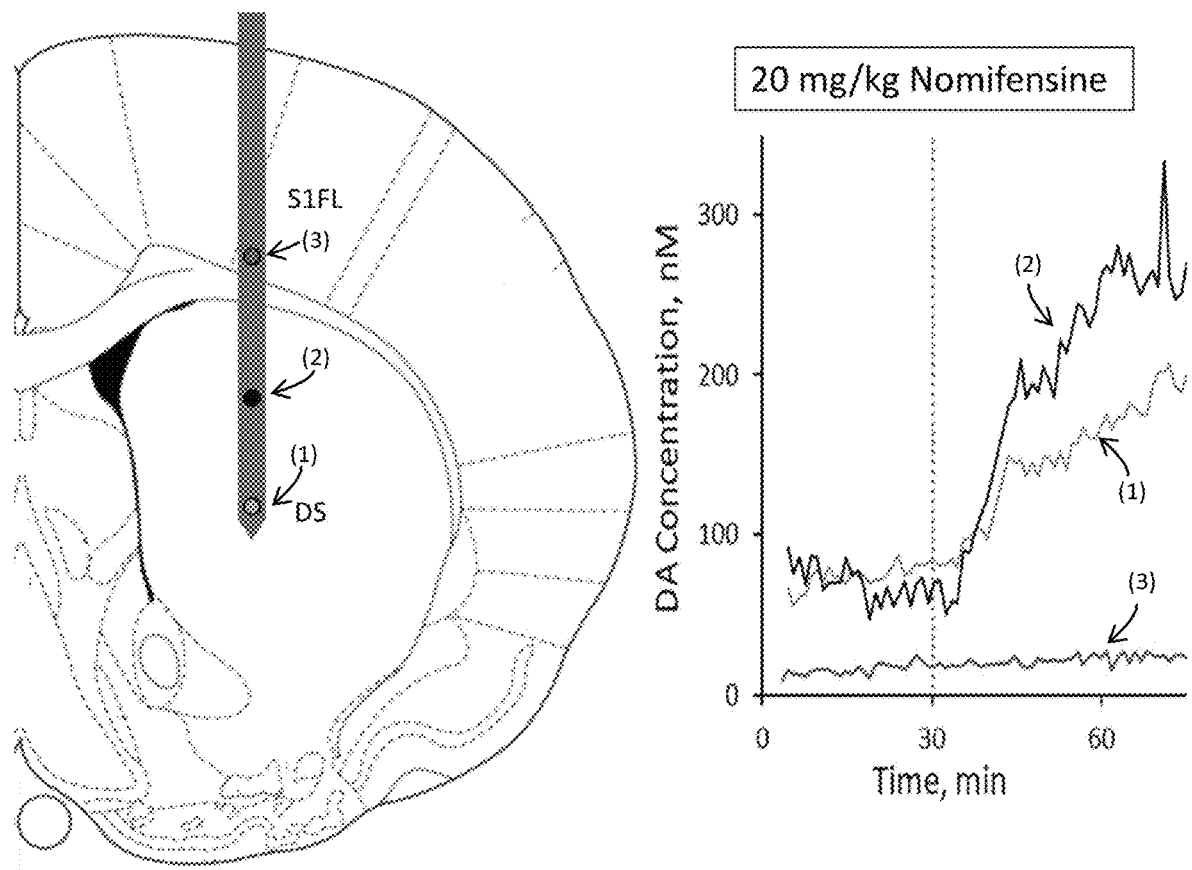
FIG. 8. PEDOT/CNT functionalized MEAs provides excellent spatio-temporal resolution for in vivo DA detection. A single silicon MEA was implanted in an anesthetized rat such that two PEDOT/CNT functionalized electrode sites were located 5.4 mm (labeled (1)) and 4.2 mm (labeled (2)) respectively below the cortical surface into the DA-rich DS while one PEDOT/CNT functionalized electrode site was located 2.6 mm (labeled (3)) below the cortical surface in the non-DA-rich forelimb region of the primary somatosensory cortex (S1FL). Both MEA electrode sites located within the DS (plots labeled (1) and (2), respectively) showed clear, nomifensine-dependent DA detection (20 mg/kg, i.p. injection at t=30 minutes, dashed vertical line), whereas the electrode located within the S1FL (plot labeled (3)) shows no nomifensine-dependent DA detection.

Motivated by the excellent in vitro performance of PEDOT/CNT coated MEAs, a proof-of-principle in vivo experiment was performed in an isoflurane anesthetized rat to show the spatial resolution afforded by measuring basal DA at a silicon based MEA. Three individual gold electrode sites were polymerized along the MEA spanning a 2.8 mm vertical distance with the middle electrode located 1.2 mm from the ventral-most electrode. The MEA was positioned above the DS (2.5 mm lateral and 0.43 mm anterior to bregma) and lowered to a final position 5.4 mm below the cortical surface (see drawing in FIG. 8) such that two of the PEDOT/CNT coated electrodes sites were located in the DA-rich DS (FIG. 8, positions labeled (1) and (2)) while the last coated electrode site was located in the non-DA-rich forelimb region of the primary somatosensory cortex (S1FL, FIG. 8, position marked (3)). Upon finalizing MEA implantation, the electrical circuit was completed with the Ag/AgCl reference and bone screw counter electrode as detailed previously. Once the electrodes were in place, the SWV waveform was repeatedly applied to each individual electrode in succession over a period of 90 minutes. We mimicked the previous in vivo experimental design by injecting 20 mg/kg, i.p. nomifensine following 30 minutes of baseline collection (FIG. 8, dashed vertical line). The two PEDOT/CNT coated gold MEA electrode sites located within the DS (positions labeled (1) and (2)) each exhibited clear DA detection as well as a site specific corresponding increase in basal DA following i.p. nomifensine administration. In all, both responses are similar to those observed at PEDOT/CNT coated CFEs (FIG. 6B). Conversely, the electrode located within the non-DA-rich S1FL does not observe a clear DA peak, nor does it observe a current change upon i.p. nomifensine administration. This proof-of-principle in vivo experiment illustrates the power of incorporating the DA sensitive PEDOT/CNT coating onto multiple electrode sites along an MEA substrate. The PEDOT/CNT coated MEA was not only able to successfully discriminate between two discrete brain regions, but it was also able to resolve two spatially discrete neuron groupings within the DS by observing distinct DA responses to nomifensine administration. Recording from spatially isolated electrode sites located both within- and between brain regions provides a depth of information regarding the chemistry of multiple specific neuron groupings. Overall, these findings represent the first ever time-correlated, multisite quantification of basal DA in the brain.

CONCLUSIONS

The ability to detect resting DA at a variety of PEDOT/CNT coated electrode sites using SWV stands as a substantial improvement to the current state of the art of neurochemical sensing. Electrodeposition of PEDOT/CNT allows for the conversion of widely used electrode materials (CFEs, MEAs, etc.) into highly sensitive and selective DA sensors. In fact, PEDOT/CNT functionalization was able to convert previously DA insensitive gold MEA electrode sites into functional DA sensing electrodes. The ease in which the DA sensing technology was transferred between substrates indicates that this DA sensing technology can readily be applied to any conductive substrate. In practice, this gives the user ultimate flexibility in developing a PEDOT/CNT based DA sensor custom designed to fit his/her specific need. Accordingly, the technology can be expanded to allow for chronic basal DA measurement and simultaneous multisite recording.

REFERENCES FOR EXAMPLE 1

Alba et al., Biosensors 5, 618, 2015
Atcherley et al., *Langmuir,* 29, 14885-14892, 2013
Atcherley, et al., *ACS Chem Neurosci,* 6, 1509-1516, 2015a
Atcherley et al., *Chem Commun,* 51, 2235-2238, 2015b
Auclair et al., *J Neuroscience,* 22, 9150-9154, 2002
Bard and Faulkner. (2001). Electrochemical Methods: Fundamentals and Applications, 2 edn (Hoboken, N.J.: John Wiley & Sons, Inc.).
Bassareo et al., *Behav Brain Res,* 287, 200-206, 2015
Bath et al., *Anal Chem,* 72, 5994-6002, 2000
Borland and Michael, *J. Neurochem.,* 91, 220-229, 2004
Borland et al., *J Neurosci Methods,* 146, 149-158, 2005
Brooks, *J Neural Transm,* 108, 1283-1298, 2001
Burrel et al., *ACS Chem Neurosci,* 6, 1802-1812, 2015
Carboni et al., *Neuroscience,* 28, 653-661, 1989
Carboni et al., *J Neuroscience,* 21, RC141, 2001
Di Chiara et al., *Neuroscience,* 55, 451-456, 1993
Du, Bi, and Cui, *Adv Funct Mater,* 28, 1703988, 2018
Floresco et al., *Nat Neurosci,* 6, 968-973, 2003
Grace, *Neuroscience,* 41, 1-24, 1991
Grace, *Nat Rev Neurosci,* 17, 524-532, 2016
Gu et al., *Anal Chem,* 87, 6088-6094, 2015
Hull et al., *Behav Brain Res,* 105, 105-116, 1999
Jaquins-Gerstl and Michael, *J Neurosci Methods,* 183, 127-135, 2009
Jaquins-Gerstl et al., *Anal Chem,* 83, 7662-7667, 2011
Johnson, Franklin, Gibson, Brown, and Kipke, *J Neurosci Methods,* 174, 62-70, 2008.
Johnson et al., *Anal. Chem.,* 90, 7181-7189, 2018
Kozai et al., *ACS Chem. Neurosci.,* 6, 48-67, 2015
Kozai et al., *IEEE transactions on bio-medical engineering,* 63, 111-119, 2016
Lourenço et al., *Sensors Actuators B: Chem,* 237, 298-307, 2016
Luo et al., *Biomaterials,* 32, 5551-5557, 2011
Nesbitt et al., *Anal Chem,* 85, 8173-8179, 2013
Nesbitt et al., *ACS Chem Neurosci,* 6, 163-173, 2015

Obien et al., *Front Neurosci*, 8: 423, 2015
Oh et al., *Anal Chem*, 88(22): 10962-10970, 2016
Oh et al., *Biosens. Bioelectron.* 121, 174-182, 2018
Osteryoung and Osteryoung, *Anal Chem*, 57, 101-110, 1985
Park, Takmakov, and Wightman, *J Neurochem*, 119, 932-944, 2011
Paxinos and Watson, (1998). The Rat Brain in Stereotaxic Coordinates (New York, N.Y.: Academic Press).
Pontieri, Tanda, and Di Chiara, *Proc Natl Acad Sci USA*, 92, 12304-12308, 1995
Ramaley and Krause, *Anal Chem*, 41, 1362-1365, 1969
Rassoulpour et al., *J Neurochem*, 93, 762-765, 2005
Robinson et al., *Clin Chem*, 49, 1763-1773, 2003
Rutherford et al., *J Neurochem*, 102, 712-722, 2007
Schmidt et al., *ACS Nano*, 7, 7864-7873, 2013
Schultz, *J Neurophysiol*, 80, 1-27, 1998
Schultz, *Annu Rev Neurosci*, 30, 259-288, 2007
Smith, Olson, and Justice Jr., *J Neurosci Methods*, 44, 33-41, 1992
Taylor et al., *J Mater Chem B*, 5, 2445-2458, 2017a
Taylor, Ilitchev, and Michael, *ACS Chem Neurosci*, 4, 870-878, 2013
Taylor et al., *J Neurochem*, 122, 283-294, 2012
Taylor et al., *J Neurochem*, 133, 522-531, 2015
Taylor et al., *Biosens Bioelectron*, 89, Part 1, 400-410, 2017b
Troyer et al., *Curr Opin Chem Biol*, 6, 696-703, 2002
Tseng and Monbouquette, *J Electroanal Chem*, 682, 141-146, 2012
Urban et al., Psychopharmacology (Berl), 221, 67-77, 2012
Varner, Jaquins-Gerstl, and Michael, *ACS Chem Neurosci*, 7, 728-736, 2016
Vasylieva et al., *Biosens Bioelectron*, 72, 148-155, 2015
Venton, Troyer, and Wightman, *Anal Chem*, 74, 539-546, 2002
Weaver et al., *J Mater Chem B*, 2, 5209-5219, 2014
Wightman, May, and Michael, *Anal Chem*, 60, 769A-779A, 1988
Wu, Rassoulpour, and Schwarcz, *J Neural Transm*, 114, 33-41, 2007
Xu et al., *Sensors Actuators B: Chem*, 188, 405-410, 2013
Yonghong et al., *Electroanalysis*, 23, 2832-2838, 2011
Zetterström et al., *Eur J Pharmacol*, 148, 327-334, 1988

It will be apparent that the precise details of the methods or compositions described may be varied or modified without departing from the spirit of the described embodiments. We claim all such modifications and variations that fall within the scope and spirit of the claims below.

We claim:

1. A method for determining dopamine concentration at a target location in neural tissue, comprising:
   measuring current level in response to square wave voltammetry with a coated electrode of a neural probe implanted at the target location, wherein the target location is selected from the group consisting of the dorsal striatum, the nucleus accumbens core, the nucleus accumbens shell, the prefrontal cortex, and the amygdala, wherein the coated electrode comprises a coating of poly 3,4 ethylene dioxythiophene (PEDOT) doped with negatively charged carbon nanotubes (CNT); and
   comparing the measured current level to a control current level to determine the dopamine concentration at the target location.

2. The method of claim 1, wherein the method determines the tonic dopamine concentration at the target location.

3. The method of claim 1, wherein the CNTs in the coating are from about 10 to about 20 nm in diameter and from about 10 to about 30 μm in length.

4. The method of claim 1, wherein the coating is electrodeposited onto the electrode.

5. A method for determining dopamine concentration at a target location in neural tissue, comprising:
   measuring current level in response to square wave voltammetry with a coated electrode of a neural probe implanted at the target location, wherein the coated electrode comprises a coating of poly 3,4 ethylene dioxythiophene (PEDOT) doped with negatively charged carbon nanotubes (CNT) that is electrodeposited onto the electrode with from about 5 to about 200 mC/cm$^2$; and
   comparing the measured current level to a control current level to determine the dopamine concentration at the target location.

6. The method of claim 5, wherein the coating is electrodeposited onto the electrode with about 100 mC/cm$^2$.

7. The method of claim 1, wherein the control current level is a current level measured for a known concentration of dopamine in response to square wave voltammetry applied with a control electrode.

8. The method of claim 1, wherein the electrode is a carbon-fiber or gold electrode.

9. The method of claim 1, wherein sweeps of the square wave voltammetry are performed at 25 Hz and lasting for about 3 seconds in length.

10. The method of claim 1, wherein sweeps of the square wave voltammetry comprise from about −0.2 to about 0.3 volts.

11. The method of claim 10, wherein the current level measured in response to application of from about −0.2 to about 0.3 volts with the neural probe is compared with the control current level to determine the dopamine concentration at the target location.

12. The method of claim 11, wherein the current level measured in response to application of about 0.18 volts with the neural probe is compared with the control current level to determine the dopamine concentration at the target location.

13. The method of claim 1, wherein the target location is neural tissue with a norepinephrine concentration of less than 1 μM.

14. The method of claim 5, wherein the target location is neural tissue with a norepinephrine concentration of less than 1 μM.

15. The method of claim 1, wherein the neural probe comprises more than one of the PEDOT/CNT coated electrodes.

16. The method of claim 15, wherein the method comprises measuring dopamine concentration at one or more target locations in the neural tissue with the PEDOT/CNT coated electrodes.

17. The method of claim 1, further comprising implanting the neural probe at the target location.

18. The method of claim 1, further comprising connecting the neural probe to a recording apparatus via one or more electrical leads; and recording and/or stimulating the neural signal from the neuronal tissue.

* * * * *